(12) United States Patent
Axelrud et al.

(10) Patent No.: US 8,521,310 B2
(45) Date of Patent: Aug. 27, 2013

(54) INTEGRATED MODEL PREDICTIVE CONTROL OF DISTILLATION AND DEHYDRATION SUB-PROCESSES IN A BIOFUEL PRODUCTION PROCESS

(75) Inventors: Celso Axelrud, Round Rock, TX (US); Maina A. Macharia, Round Rock, TX (US); Michael E. Tay, Georgetown, TX (US)

(73) Assignee: Rockwell Automation Technologies, Inc., Mayfield Heights, OH (US)

(*) Notice: Subject to any disclaimer, the term of this patent is extended or adjusted under 35 U.S.C. 154(b) by 836 days.

(21) Appl. No.: 11/862,391

(22) Filed: Sep. 27, 2007

(65) Prior Publication Data
US 2008/0103748 A1 May 1, 2008

(51) Int. Cl.
- *G05B 13/04* (2006.01)
- *C12M 1/36* (2006.01)
- *C12M 1/34* (2006.01)
- *C12M 1/00* (2006.01)

(52) U.S. Cl.
CPC ............. *G05B 13/04* (2013.01); *C12M 41/48* (2013.01); *C12M 41/00* (2013.01); *C12M 43/02* (2013.01); *C12M 47/10* (2013.01); *Y10S 203/19* (2013.01)
USPC ............. 700/29; 700/32; 700/33; 700/45; 700/50; 703/11; 203/DIG. 18

(58) Field of Classification Search
None
See application file for complete search history.

(56) References Cited

U.S. PATENT DOCUMENTS

| | | | | |
|---|---|---|---|---|
| 4,309,254 | A | * | 1/1982 | Dahlstrom et al. ............. 203/47 |
| 4,358,346 | A | | 11/1982 | Shinskey |
| 4,626,321 | A | * | 12/1986 | Grethlein et al. .............. 203/26 |
| 5,058,043 | A | * | 10/1991 | Skeirik ......................... 700/167 |
| 5,177,008 | A | * | 1/1993 | Kampen ........................ 435/139 |
| 5,407,817 | A | * | 4/1995 | Lightsey et al. .............. 435/165 |
| 5,477,444 | A | * | 12/1995 | Bhat et al. ........................ 700/48 |
| 5,932,456 | A | * | 8/1999 | Van Draanen et al. ....... 435/144 |
| 6,510,368 | B1 | * | 1/2003 | Beardwood et al. .......... 700/266 |
| 6,609,119 | B1 | * | 8/2003 | Meghlaoui ...................... 706/25 |

(Continued)

OTHER PUBLICATIONS

Grosman, B. & Lewin, D. R. Automated nonlinear model predictive control using genetic programming. Computers & Chemical Engineering 26, 631-640 (2002).*

(Continued)

*Primary Examiner* — Soren Harward
(74) *Attorney, Agent, or Firm* — Fletcher Yoder, P.C.; William R. Walbrun; John M. Miller

(57) ABSTRACT

A system and method are provided for integrated management of a biofuel distillation process and a biofuel dehydration process of a biofuel production process, comprising a dynamic multivariate model-based controller coupled to a dynamic multivariate predictive model. The model is executable to: receive distillation and dehydration process information including biofuel compositions, receive an objective for biofuel production output from the distillation and dehydration processes, e.g., target product composition, production rate, and/or feed rate, and generate model output comprising target values for a plurality of manipulated variables related to the distillation and dehydration processes in accordance with the objective. The controller is operable to dynamically control the biofuel production process by adjusting the plurality of manipulated variables to the model-determined target values in accordance with the objective for biofuel production.

22 Claims, 7 Drawing Sheets

(56) References Cited

U.S. PATENT DOCUMENTS

| | | | |
|---|---|---|---|
| 6,792,336 B1* | 9/2004 | Johnson et al. | 700/266 |
| 6,934,931 B2* | 8/2005 | Plumer et al. | 717/104 |
| 2002/0077711 A1 | 6/2002 | Nixon et al. | |
| 2004/0023349 A1* | 2/2004 | Bisgaard-Frantzen et al. | 435/161 |
| 2005/0112739 A1* | 5/2005 | Golubkov | 435/161 |
| 2005/0233030 A1* | 10/2005 | Lewis et al. | 426/49 |
| 2007/0078530 A1* | 4/2007 | Blevins et al. | 700/29 |
| 2007/0089356 A1* | 4/2007 | Krasutsky et al. | 44/605 |
| 2008/0103747 A1 | 5/2008 | Macharia et al. | |
| 2008/0104003 A1 | 5/2008 | Macharia et al. | |
| 2008/0108048 A1 | 5/2008 | Bartee et al. | |
| 2008/0109100 A1 | 5/2008 | Macharia et al. | |
| 2008/0109200 A1 | 5/2008 | Bartee et al. | |
| 2008/0167852 A1 | 7/2008 | Bartee et al. | |

OTHER PUBLICATIONS

Henson, M. Nonlinear model predictive control: current status and future directions. Computers & Chemical Engineering 23, 187-202 (1998).*

Kamm, B. & Kamm, M. Principles of biorefineries. Applied Microbiology and Biotechnology 64, 137-145 (2004).*

Miao, Q. & Wang, S.-F. Nonlinear model predictive control based on support vector regression. In 2002 International Conference on Machine Learning and Cybernetics, 2002, vol. 3, 1657-1661 vol. 3 (2003).*

Piche, S., Sayyar-Rodsari, B., Johnson, D. & Gerules, M. Nonlinear model predictive control using neural networks. Control Systems Magazine, IEEE 20, 53-62 (2002).*

Qin, S. A survey of industrial model predictive control technology. Control Engineering Practice 11, 733-764 (2003).*

Raiko, T. & Tornio, M. Learning nonlinear state-space models for control. In Proceedings. 2005 IEEE International Joint Conference on Neural Networks, 2005. IJCNN '05., vol. 2, 815-820 (2005).*

Onogi, K., Nishimura, Y., Nakata, Y. & Inomata, T. An on-line operating control system for a class of combined batch/semi-continuous processes. Journal of Chemical Engineering of Japan 19, 542-548 (1986).*

Djavdan, P. Design of an on-line scheduling strategy for a combined batch/continuous plant using simulation. Computers & Chemical Engineering 17, 561-567 (1993).*

De Filippis P. et al: "Transesterification Processes for Vegetable Oils: A Simple Control Method of Methyl Ester Content": Journal of the American Oil Chemists' Society, Springer, [Online] vol. 72, No. 11, Nov. 1999; pp. 1399-1404; URL:http:/www.springerlink.com/content/content/104526532m44217/> [retrieved on Apr. 7, 2008] p. 1399-p. 1403.

Zagonel, G. F. et al: "Multivariate Monitoring of Soybean Oil Ethanolysis by FTIR"; TALANTA, [Online] vol. 63, No. 4, Jul. 8, 2004, pp. 1021-1025, XP002475272; ISSN: 0039-9140; URL:http://www.sciencedirect.com/science/article/B6TH-4BYC4WP-3/2/61e114baa27283edf55610a541e1a626> [retrieved on Apr. 7, 2008] p. 1021-p. 1022.

Ghesti, G. F. et al: "Application of Raman Spectroscopy to Monitor and Quantify Ethyl Esters in Soybean Oil Transesterification"; Journal of the American Oil Chemists' Society, [Online] vol. 83, No. 7, Jul. 2006, pp. 597-601, XP002475273; Berlin / Heidelbert; ISSN: 0003-021X; Retrieved from the Internet: URL: http://www.springerlink.com/content/1h026742u8661135/> [retrieved on Apr. 7, 2008] p. 597-p. 600.

U.S. Appl. No. 12/052,117, Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.
U.S. Appl. No. 12/242,531, filed Sep. 30, 2008, Macharia et al.
U.S. Appl. No. 12/242,568, filed Sep. 30, 2008, Macharia et al.
U.S. Appl. No. 12/242,606, filed Sep. 30, 2008, Macharia et al.
U.S. Appl. No. 12/242,635, filed Sep. 30, 2008, Macharia et al.

* cited by examiner

INTEGRATED MODEL PREDICTIVE CONTROL OF DISTILLATION AND DEHYDRATION SUB-PROCESSES IN A BIOFUEL PRODUCTION PROCESS

PRIORITY DATA

This application claims benefit of priority of U.S. provisional application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee.

FIELD OF THE INVENTION

The present invention generally relates to the field of model predictive control of production processes for biofuel and its co-products. More particularly, the present invention relates to systems and methods for integrated model predictive control of distillation and dehydration sub-processes in a biofuel production process.

DESCRIPTION OF THE RELATED ART

History of Biofuel

Biofuel refers to any fuel derived from biomass, i.e., from recently living organisms or their bi-products. Biofuels were used in automobiles from approximately 1876-1908. The Otto Cycle (1876) was the first combustion engine designed to use alcohol and gasoline. Henry Ford's Model T (1908) was designed to use biofuel, gasoline, or any combination of the two fuels. However, high government tariffs on alcohol discouraged the use of biofuel, and gasoline became the predominant fuel choice for automobiles for many decades.

The energy crisis of the 1970s renewed the search for an alternative to fossil fuels. The Energy Tax Act of 1978 (H.R. 5263) provided a 4 cents per gallon exemption from Federal excise taxes to motor fuels blended with biofuel (minimum 10 percent biofuel) and granted a 10% energy investment tax credit for biomass-biofuel conversion equipment (in addition to the 10% investment tax credit available) that encouraged plant building. However, by 1985, only 45% of the 163 existing commercial biofuel plants were operational. This high plant failure rate was partially the result of poor business judgment and inefficient engineering design. In 1988, biofuel was used as an oxygenate in Denver, Colo., which mandated the use of oxygenated fuels during winter use. Oxygenated fuels are fuels that have been infused with oxygen to reduce carbon monoxide emissions and NOx emissions created during the burning of the fuel. The Clean Air Act in the 1990s, motivated an additional increase in the use of biofuel as a pollution control additive.

The US Congress passed the Clean Air Act Amendments of 1990, which mandated the use of "reformulated gasoline" containing oxygenates in high-pollution areas. Starting in 1992, Methyl Tertiary Butyl Ether (MTBE) was added to gasoline in higher concentrations in accordance with the Clean Air Act Amendments. Improvements in air quality in many areas has been attributed to the use of gas reformulated with MBTE. However by 2000, MTBE—(a known carcinogenic agent) was found to have contaminated groundwater systems, mostly through leaks in underground gasoline storage tanks. In 2004, California and New York banned MTBE, generally replacing it with ethanol. Several other states started switching soon afterward. The 2005 Energy Bill required a phase out of MTBE and did not provide legal protection for the oil companies. As a result, the oil companies began to replace MTBE with ethanol (one embodiment of a biofuel), thereby spurring growth in the biofuels industry.

Since 2001, there has been a steady rise in crude oil prices that has increased the price of gasoline above the break-even point of biofuel's cost of production. This has been very beneficial to Mid-west agricultural regions that have always sought ways to diversify demand for agricultural goods and services. Biofuel plants that had depended on subsidies to be profitable are now transitioning to an economically viable venture for this corn-rich region.

Biofuel Production Plants

An exemplary high-level design of a biofuel production plant or process is shown in FIG. 1, which illustrates how biomass is processed through several stages to produce biofuel and one or more co-products. Biomass is first provided to a milling and cooking process, e.g., milling and cooking units 104, where water 102 (and possibly recycled water RW1 and RW2) is added and the biomass is broken down to increase the surface area to volume ratio. This increase in surface area allows for sufficient interaction of the water and biomass surface area to achieve a solution of fermentable sugars in water. The mixture, a biomass and water slurry, is cooked to promote an increase in the amount of contact between the biomass and water in solution and to increase the separation of carbohydrate biomass from the non-carbohydrate biomass. The output of the milling and cooking units 104 (i.e., the fermentation feed or mash) is then sent to a fermentation process, where one or more fermentation units 106 operate to ferment the biomass/water mash produced by the milling and cooking process.

As FIG. 1 indicates, the fermentation process may require additional water 102 to control the consistency of material to the fermentation units (also referred to herein as a fermenter). Biomass is converted by yeast and enzymes into a biofuel and by-products such as carbon dioxide, water and non-fermentable biomass (solids), in the fermentation units 106.

The output from the fermentation units 106 is sent to a distillation process, e.g., one or more distillation units 108, to separate biofuel from water, carbon dioxide, and non-fermentable solids. If the biofuel has to be dehydrated to moisture levels less than 5% by volume, the biofuel can be processed through a processing unit called a molecular sieve or similar processing units (including, for example, additive distillation such as cyclohexane that breaks a water/ethanol azeotrope). The finalized biofuel is then processed to ensure it is denatured and not used for human-consumption.

The distillation units 108 separate the biofuel from water. Water 102 is used in the form of steam for heat and separation, and the condensed water is recycled (RW1) back to the milling and cooking units 104, as shown in FIG. 1. Stillage (non-fermentable solids and yeast residue), the heaviest output of the distillation units, is sent to stillage processing for further development of co-products from the biofuel production process.

Stillage processing units 110 separate additional water from the cake solids and recycle this water (RW2) back to the milling and cooking units 104. There are a number of stillage processing options: stillage can be sold with minimal processing, or further processed by separating moisture from the solids product via one or more centrifuge units. From the centrifuge, the non-fermentable solids may be transported to dryers for further moisture removal. A portion of the stillage liquid (centrate) may be recycled back to the fermentation units 106; however, the bulk of the flow is generally sent to evaporator units, where more liquid is separated form the liquid stream, causing the liquid stream to concentrate into syrup, while solid stillage is sent to a drying process, e.g., using a drying unit or evaporator, to dry the solid stillage to a specified water content. The syrup is then sent to the syrup tank. Syrup in inventory can be processed/utilized with a number of options: it can be sprayed in dryers to achieve a specified color or moisture content; it can be added to the partially dried stillage product, or it can be is sold as a separate liquid product. The evaporator unit may have a water by-product stream that is recycled back to the front end (RW2), e.g., to the milling and cooking units 104.

Note that an energy center 112 supplies energy to various of the processing units, e.g., the milling and cooking units 104, the distillation 108 and mole-sieve units, and the stillage processing units. The energy center 112 may constitute a thermal oxidizer unit & heat recovery steam generator that destroys volatile organic compounds (VOCs) and provides steam to the evaporators, distillation units 108, cooking system units (e.g., in 104), and dehydration units. The energy center 112 is typically the largest source of heat in the biofuels plant In prior art biofuel plants, properties such as temperature or product quality are controlled with control systems utilizing traditional control schemes such as temperature, pressure, level, and/or flow control schemes, which may include proportional integral derivative (PID), cascade, feedfoward, and/or constraint control schemes, among others.

Systems can be open or closed. An open loop system is a system that responds to an input, but the system is not modified because of the behavior of the output. FIG. 2 illustrates a generic open loop process/system 202, where the process/system 202 receives process input, and generates process output, with no feedback from output back to input. Open loop systems are only defined by the inputs and the inherent characteristics of the system or process. In the biofuel production process, the system may comprise the entire bio-processing plant, one process section of the bio-processing plant, such as the milling and cooking units, or a controller for a variable in a process such as the temperature of the cooking units.

In a closed loop system, the inputs are adjusted to compensate for changes in the output, where, for example, these changes may be a deviation from the desired or targeted measurements. The closed loop system senses the change and provides a feedback signal to the process input. FIG. 3 illustrates a generic closed loop process/system where the process/system 202 receives process input and generates process output, but where at least a portion of the output is provided back to the input as feedback. Process units in the biofuel system may be closed loop systems if they need to be regulated subject to constraints such as product quality, energy costs, or process unit capacity.

Modern plants apply traditional and advanced controls to regulate complex processes to achieve a specific control objective. Traditional PID controllers and other control systems such as ratio controls, feed-forward controls, and process models may be used to control biofuel production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

Most biofuel production facilities mill or steep corn, other grains, or other biomass (e.g. sugarcane), and mix this milled carbohydrate base with water from a variety of sources and quality.

The operating challenge is to provide a steady quality and concentration of feed to the fermentation units. However, due to variability in feed amount, flow rates, mill rates, steep efficiencies, or biomass (e.g., grain) quality, the fermentation output varies dramatically and the process operates sub-optimally due to this large variability. Fermentation end concentrations of biofuel may vary plus or minus 10% or more.

Plants are currently implemented to provide some information to plant operators to enable them to increase or decrease the feed of fermentable sugar and starch concentrations to fermentation tanks. Plant operators monitor the target feed quality and percent solids in the fermentation feed and run the plants to achieve a target percent solids so that each fermentation batch is started with a rough approximation of the target percent solids and each fermentation process runs over a specific time period in an attempt to achieve an output with approximately the design target percent of biofuel. In addition, a recycle flow rate is typically managed to maintain tank inventory levels within safe operating limits, while providing sufficient water/liquid to mix with grain or other biomass solids to fill a fermentation tank within a targeted time period (i.e. fill a vessel of 180,000 gallons in 15 hours so that the fill rate would be 600 gallons per minute).

In addition, levels of various water sources tend to increase or decrease, and operators or level controllers may adjust flows to regain targeted levels. In general, these applications are controlled with flow, level or mill speed controllers (e.g., regulatory level controllers). Some applications of ratio controllers are used in current control systems (e.g., to monitor the ratio of enzyme flow rates to grain slurry flow rates).

Two additional calculated parameters are also important to plant operators. The first parameter is Percent Recycle (also referred to as backset), which is the fractional percentage of recycled thin stillage (fermentation liquor output from a centrifuge that separates out cattle feed solids). Percent Recycle is managed manually to maintain both a rough thin stillage inventory and to operate within a range of fractional percent backset. It is important to manage the fractional percent backset, because the fermentation liquor contains both residual yeast nutrients along with yeast waste products from previous fermentation. Too little or too much backset can be a problem for fermentation productivity.

The second parameter is Fermentation Inventory, which is a totalized inventory across the filling, draining and fermenting fermentation vessels and key auxiliary equipment. If this total inventory level is held within an acceptably stable band, the front plant section, i.e., the milling/cooking, and fermentation processes, can be managed to match the back plant section, i.e., the distillation and stillage processes, across all batch sequentially operated fermentation vessels. If totalized batch volume is constant, then filling is balanced with draining across multiple parallel batch fermentation vessels.

A biofuel production plant may require numerous adjustments, e.g., on a minute-to-minute basis, in response to changes and shifting constraints if the plant process is to operate in an optimal manner. Due to this complexity, human operators are not capable of actively optimizing a biofuel production process. Consequently, operators generally operate a plant in a less efficient operating mode.

Thus, improved systems and methods for biofuel production are desired.

SUMMARY OF THE INVENTION

Embodiments of a system and method are presented for managing a distillation and dehydration process in a biofuel production process. In one embodiment, the system may include a dynamic multivariate predictive model-based controller coupled to a memory storing a dynamic multivariate predictive model of integrated distillation and dehydration sub-processes of the biofuel production process.

In some embodiments, the controller includes dynamic control models that link all process interactions between the dehydration and the distillation sub-processes. With these model relationships the system may manage the control objective and effectively manipulate each sub-process to respond to changing conditions in the other. This way the controller may manage a control objective that is global to both sub-processes. Any changes to distillation/dehydration constraints may be globally responded to and controlled in the context of the objective function of the controller.

The dynamic multivariate predictive model-based controller may be executable to: receive process information from the biofuel production process; receive an objective for the distillation and dehydration sub-processes specifying at least one measurable attribute defining biofuel output product quality for the distillation and dehydration process; and execute the integrated dynamic multivariate predictive model to generate model output comprising target values for a plurality of manipulated variables related to the distillation and dehydration sub-processes in accordance with the specified objective. In some embodiments, the target values may include or be one or more trajectories of values over a time horizon, e.g., over a prediction or control horizon.

The dynamic multivariate predictive model-based controller may be operable to dynamically control the biofuel production process by communicating target values for the plurality of manipulated variables to a distributed process control system that may adjust the manipulated variables to achieve the target values within a determined time horizon. The distributed process control system may then communicate the new values for the manipulated variables and control variables to the dynamic multivariate predictive model-based controller, and the process may be repeated as appropriate to achieve the desired control of the biofuel production process.

In one embodiment, the method may include providing an integrated dynamic multivariate predictive model of the distillation and dehydration processes of the biofuel production process; receiving an objective for the distillation and dehydration processes specifying target production of the biofuel output of the distillation and dehydration processes, which may include one or more of: a target composition of the biofuel output of the distillation and dehydration processes, a production rate of the biofuel output of the distillation and dehydration processes (e.g., production rate of one or more distillation and dehydration units), or a target feed rate of the distillation and dehydration processes (i.e., input feed rate of one or more distillation and dehydration units); receiving process information from the biofuel production process; executing the integrated dynamic multivariate predictive model in accordance with the objective using the received process information as input, to generate model output including target values for a plurality of manipulated variables related to the distillation and dehydration processes, in accordance with the objective; and controlling the biofuel production process, in accordance with the target values of the plurality of manipulated variables to control biofuel composition in accordance with the objective.

In some embodiments, the integrated dynamic multivariate predictive model may include one or more of: a linear model, a nonlinear model, a fundamental model, an empirical model, a neural network, a support vector machine, a statistical model, a rule-based model, or a fitted model. For example, in some embodiments where a hybrid approach is used, the integrated dynamic multivariate predictive model may include a fundamental model (e.g., a model based on chemical and/or physical equations) plus one or more of: a linear empirical model, a nonlinear empirical model, a neural network, a support vector machine, a statistical model, a rule-based model, or an otherwise empirically fitted model.

In some embodiments, the execution of the integrated dynamic multivariate predictive model may include executing the model in an iterative manner, e.g., via an optimizer, e.g., a nonlinear optimizer, varying manipulated variable values (which are a subset of the model inputs) and assessing the resulting model outputs according to the objective, to determine target values of the manipulated variables that satisfy the objective over a determined time horizon.

In some embodiments, the method may further include: receiving constraint information specifying one or more constraints; and executing the integrated dynamic multivariate predictive model in accordance with the objective using the received process information and the one or more constraints as input, to generate model output in accordance with the objective and subject to the one or more constraints.

In some embodiments, the integrated dynamic multivariate predictive model may specify relationships between biofuel output composition and equipment constraints of the biofuel production process, the dynamic multivariate predictive model-based controller may receive the one or more equipment constraints as input, and the target values for the manipulated variables may be computed to approach and maintain the target biofuel output composition subject to the one or more equipment constraints.

In some embodiments, the objective for the distillation and dehydration processes may be specified by a human operator and/or a program.

BRIEF DESCRIPTION OF THE DRAWINGS

A better understanding of the present invention can be obtained when the following detailed description of the preferred embodiment is considered in conjunction with the following drawings, in which.

Figure 1:
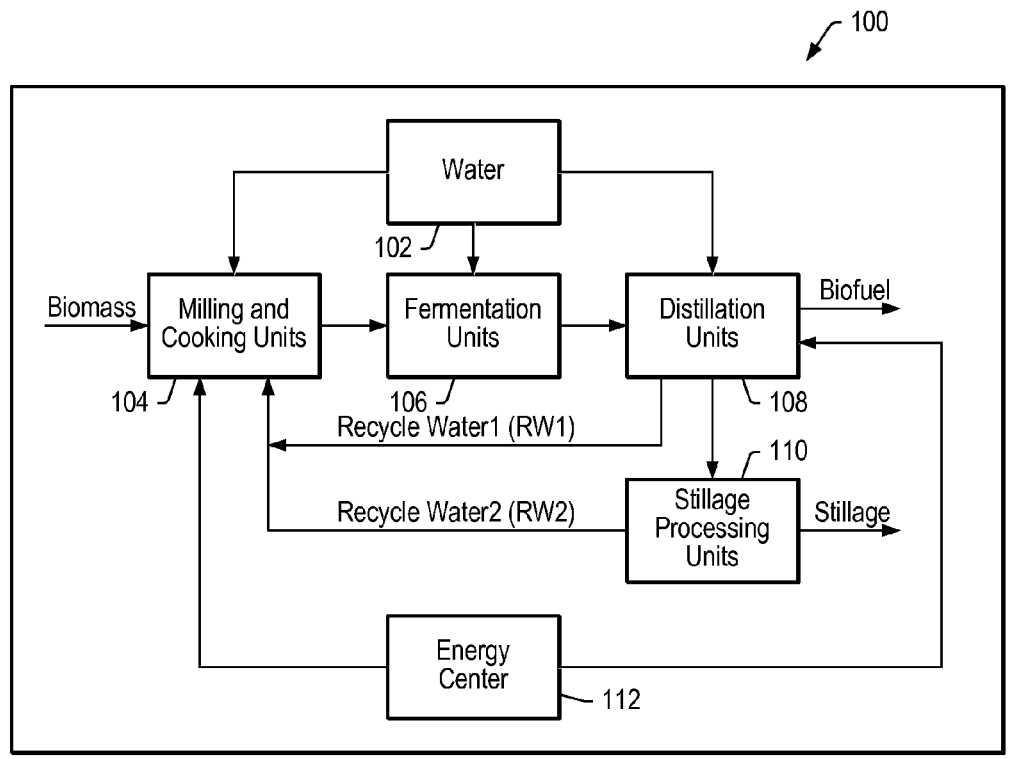
FIG. 1 illustrates one example of a biofuel processing plant, according to the prior art.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Incorporation by Reference

The following references are hereby incorporated by reference in their entirety as though fully and completely set forth herein:

U.S. provisional application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee.

Definitions—Biofuel Production Processes

Biofuel—any fuel (or fuels) derived from biomass, i.e., from recently living organisms or their bi-products.

Biofuel production process—a fermentation process surrounded by auxiliary processing units to produce biofuel, other fermentable alcohols for fuel, and high-capacity food grade or chemical grade alcohols.

Biofuel production—a measure of biofuel production within or at the end of a production process. May include measurements such as concentration (e.g., wt. %, volume % or wt./vol. %), volume (e.g., current gallons biofuel within a fermenter) or mass (e.g., current kg biofuel within a fermenter).

Batch processing—a staged discontinuous processing step that includes a start and an end, in contrast to continuous processing that continues without stop, e.g., during a normal operating day or week. Continuous processing is generally represented by fairly steady targets or operations, where at least some parameters change throughout batch processing. For example, biofuel production, e.g., fermentation, starts at low levels at the start of a batch and increases throughout the batch with or without a drop at the end representing degradation rates being higher than production rates. Similarly, yeast cellular concentrations, start at fairly low levels, and generally grow throughout a batch, although they generally have a lag (relatively constant concentrations), exponential growth, stable growth, and degradation phase within a batch.

Slurry—a fermentation feed mash comprising a two-phase (liquid and solid) slurry that will be fermented.

Solids or % solids—fraction or percent of solids in the fermentation feed.

Milling and Cooking Process—continuous processing for pre-fermentation of the fermentation feed, which generally includes grain or cane milling, cooking, mixing with water and processing chemicals, cooking for sterilization and increasing water concentration within solids, and other pre-fermentation processing.

Biomass concentration—content attribute of the fermentation feed specified by one or more of: slurry solids, liquefaction solids, slurry density, liquefaction density, slurry % or fraction carbohydrates, and slurry % or fraction fermentable sugar.

Liquids inventory information—includes water flows, recycle liquid flows, evaporator condensate recycle flow, thin stillage or centrifuge liquor recycle flows, water addition flows, processed water addition flows, slurry flows, mash flows, and various levels or weights for various tanks used to hold inventories of these flows or for intermediate receptacles (e.g. methanator feed tank, slurry feed tank, liquefaction tank, distillate tank, grain silo inventories or other biomass inventories, etc.).

Liquefaction—for grains with high starch content, the starch is liquefied to reduce its carbohydrate chain length and viscosity by adding enzymes or other biologic agents.

Thermal Oxidizer/Heat Recovery Steam Generator (HRSG)—process equipment that is used to destroy volatile organic compounds (VOCs), to reduce air and remove stenches from stillage dryer or evaporation systems. The heat recovery steam generator is used to recover the heat required to destroy the VOCs, and is typically the energy center of the biofuels production process.

Dried Distillers Grains (DDG)—post fermentation solid residue that includes undigested grain residue, other solid residues (enzymes, salts), and yeasts (or other cellular residue) that may be dried and released as a production by-product (generally as animal feed). DDG may also be used herein to include WDG (wet distillers grains), which are only partially dried for local consumption (e.g. without long-term biological stability) and DDGS/WDGS (dried distillers grains with solubles and wet distillers grains with solubles). Solubles includes residue solids that are soluble in water and therefore present in stillage concentrate. Solubles may be partially concentrated (generally with evaporation), and added to DDG or WDG to increase yields and manage by-product inventories.

Enzyme—highly selective biological-based catalyst added to manage specific reactions within a fermentation process. The most common enzymes used today include alpha amylase to rapidly break starches into dextrins, gluco-amylase to break dextrins into glucose, and proteases to break grain proteins into digestible proteins to support cell growth. In the same way as described below, modeling and controlling starch-based fermentations, enzymes specific for cellulosic conversion into biofuels or other enzymes affecting yeast (see below), growth or nutrient availability may be managed.

Yeast—a biofuel producing organism. Yeasts are currently the most commonly used organism in ethanol production although other biofuel producing organisms including genetically engineered *E. coli* can be substituted throughout as the technology described may not be specific to yeast, and may apply to many organisms used in fermentation processes to produce biofuel.

Stillage/Whole Stillage—non-fermentable solids and water liquid removed from the bottom of the primary distillation units.

Thin Stillage—the separated liquid from the stillage non-fermentable solids.

Syrup—concentrated thin-stillage with a large portion of the moisture removed. The % solids in syrup are usually in the range of 20-45% solids, but percentages outside this range may occur.

Azeotrope—a special mixture of two compounds, that when in equilibrium, the vapor phase and liquid phase have exactly the same compositions. This makes it difficult to separate the two components to achieve a better purity. Special separation processes are required to break the azeotrop. They comprise azeotropic distillation (add a $3^{rd}$ compound to break the azeotrop), extractive distillation (use a solvent to separate the 2 compounds), or molecular sieve technology (preferentially trap molecules of one component in a molecular sieve bed as the other component passes over the molecular sieve bed).

Volatile Organic Compounds (VOCS)—Organic compounds that tend to vaporize when subject to atmospheric pressure and ambient temperature ranges.

Capacity—capacity is the established maximum production rate of the process, sub-process, or unit under best operating conditions (no abnormal constraints). Capacity is generally a constant within the present capital investment. For new units it is the vendor's specified capacity. For established units, capacity is established by demonstrated historical production rates.

Model—an input/output representation, which represents the relationships between changes in various model inputs and how the model inputs affect each of the model outputs.

Dynamic Predictive Model—an input/output representation of a system or process that not only reflects how much an output changes when an input is changed, but with what velocity and over what time-dependent curve an output will change based on one or more input variable changes. A dynamic multivariate predictive model is a dynamic predictive model that represents or encodes relationships among multiple parameters, and is operable to receive multiple inputs, and generate multiple outputs.

Model Predictive Control (or MPC)—use of multivariate dynamic process models to relate controller objectives (targeted controller outputs and constraints) with regulatory controllers (existing single-input/single-output controllers such as ratio flow, temperature, level, speed, or pressure controllers) over a predicted time interval (e.g., 1 minute, 30 minutes, 2 hours, 100 hours, etc.).

Objective Function—encodes an objective that sets the goal or goals for the overall operation of the process, sub-process, or unit. The objective function provides one or more consistent numerical metric(s) to which the process, sub-process, or unit strives to achieve and over which the performance of the process, sub-process, or unit may be measured, e.g., from a business.

Control Variables—(also called controlled variables) those variables that the controller/optimizer tries to bring to a specified value, e.g., to a target value, maximum, etc. The range of allowed values for each control variable may be limited by constraints.

Integrated Variables—integrated control variables are variables that are not stable, but integrate generally with a stable first derivative as a function of time. The most common integrated variable is a tank level where as long as inputs and outputs are imbalanced the level will increase or decrease. Thus, when balanced a change in an input or output flow will cause a tank to either overfill or drain as integrated over time. A controller must use these integration calculations to determine when and how rapidly input or output flows must be adjusted.

Manipulated Variables—those variables over which the management of the process or unit has authority and control, e.g., via regulation of the process with online controllers, and which are changed or manipulated by the controller/optimizer to achieve the targets or goals of the control variables. Manipulated variables may operate within some range of controllable or fixed constraints. Manage is an alternate term for process control.

Disturbance Variable—a variable representing an external influence on a process that, in addition to objective variables and regulatory controllers, is outside the controller scope, and so it acts on the objective variables, but independently of the described controller. Disturbance variables are used in feedforward disturbance rejection. Disturbance variables are also measured or unmeasured variables over which the management of the process or unit does not have direct authority or control. For example, temperature, humidity, upstream flow, or quality, may all be referred to as measured disturbance variables.

Set Point (targets)—also "setpoint"; the target signal or value for a manipulated variable or targeted controlled variable.

Constraints—Constraints represent limitations on particular operating variables or conditions that affect the achievable production rate of a production unit. Constraints are of two types: controllable and external, defined below. Constraints may include, but are not limited to: safety constraints, equipment constraints, equipment availability constraints, personnel constraints, business execution constraints, control constraints, supply chain constraints, environmental permit and legal constraints. Safety constraints ensure the safety of equipment and personnel. Equipment constraints, such as the maximum open position of a control valve, maximum tank capacity, etc., may limit the physical throughput of the unit. Equipment availability constraints may include, but are not limited to: readiness due to maintenance planning and scheduling, or due to unexpected equipment outages, authorized production level set by the supply chain and production scheduling systems. Personnel constraints refer to limitations on the availability of staffing and support functions, business rules and constraints imposed by contract and policy. Business execution constraints are limits imposed by the time required to execute associated business and contractual tasks and obligations. Control constraints are limits on the maximal position and rate of change of manipulated variables. Supply chain constraints are limits on the availability of raw materials, energy, and production supplies. Environmental permit and legal constraints are limits on air emissions, wastewater, waste disposal systems, and/or environmental constraints imposed upon the performance of the unit, such as river levels and current weather imposed limitations.

Controllable Constraints—constraints imposed on the performance of a process or unit over which the management of the process or unit does have authority and discretionary control. For example, the separation in a distillation tower may be affected by distillation tray fouling. The tray fouling is a function of how the feedstock is processed, and how often the unit is taken offline for cleanup. It is management's discretion as to when the unit is serviced. Controllable constraints change a unit's throughput capacity.

External Constraints—limitations imposed on the performance of the process, sub-process, or unit over which the management of the process, sub-process, or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

System—a system may be defined by the inputs and the characteristics of the system or process. In the biofuel production process, the system may be defined for: the entire biofuel production process, a sub-process of the biofuel production process such as the milling and cooking process, or control of a variable in a sub-process such as the cooking temperature.

Figure 2:
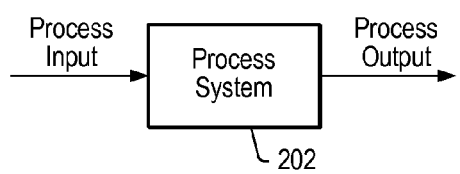
FIG. 2 illustrates an open loop process system, according to the prior art.
Figure 3:
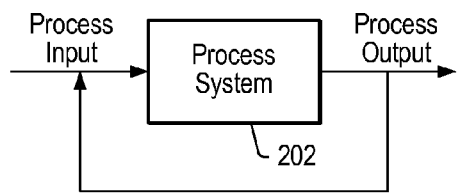
FIG. 3 illustrates a closed loop process system, according to the prior art.

Open Loop Systems—are systems that respond to an input, but the system is not modified because of the behavior of the output (see FIG. 2). For example, in a biofuel system, a reciprocating pump will operate and move at a fixed volume of syrup independent of the upstream and downstream pressure if the reciprocating pump does not have a pressure control system.

Closed Loop Systems—system inputs may be adjusted to compensate for changes in the output. These changes may be a deviation from an objective for the system, impacts of constraints on the system or system variables, or measurements of output variables. The closed loop system may be used to sense the change and feedback the signal to the process input. In biofuel systems, closed loop systems may predominate, since these systems may be regulated subject to constraints such as production (product) quality, energy costs, process unit capacity, etc.

Control System—the regulatory level mechanism by which the manipulated variables are driven to the set points.

Response—the measurement of the current position of the manipulated variable. The response is the feedback of the movement of the manipulated variable to the set point in response to the actions of the control system in its effort to achieve the set point.

Target Profile—a desired profile or trajectory of variable values, i.e., a desired behavior of a control variable or a manipulated variable.

Control Horizon—the period of the time extending from the present into the future during which one plans to move or change manipulated variables. Beyond this horizon the MV is assumed to stay constant at its last or most recent value in the control horizon.

Prediction Horizon—the period of time extending from the present into the future during which the process or system response is monitored and compared to a desired behavior.

Biofuel Production Process

Figure 4:
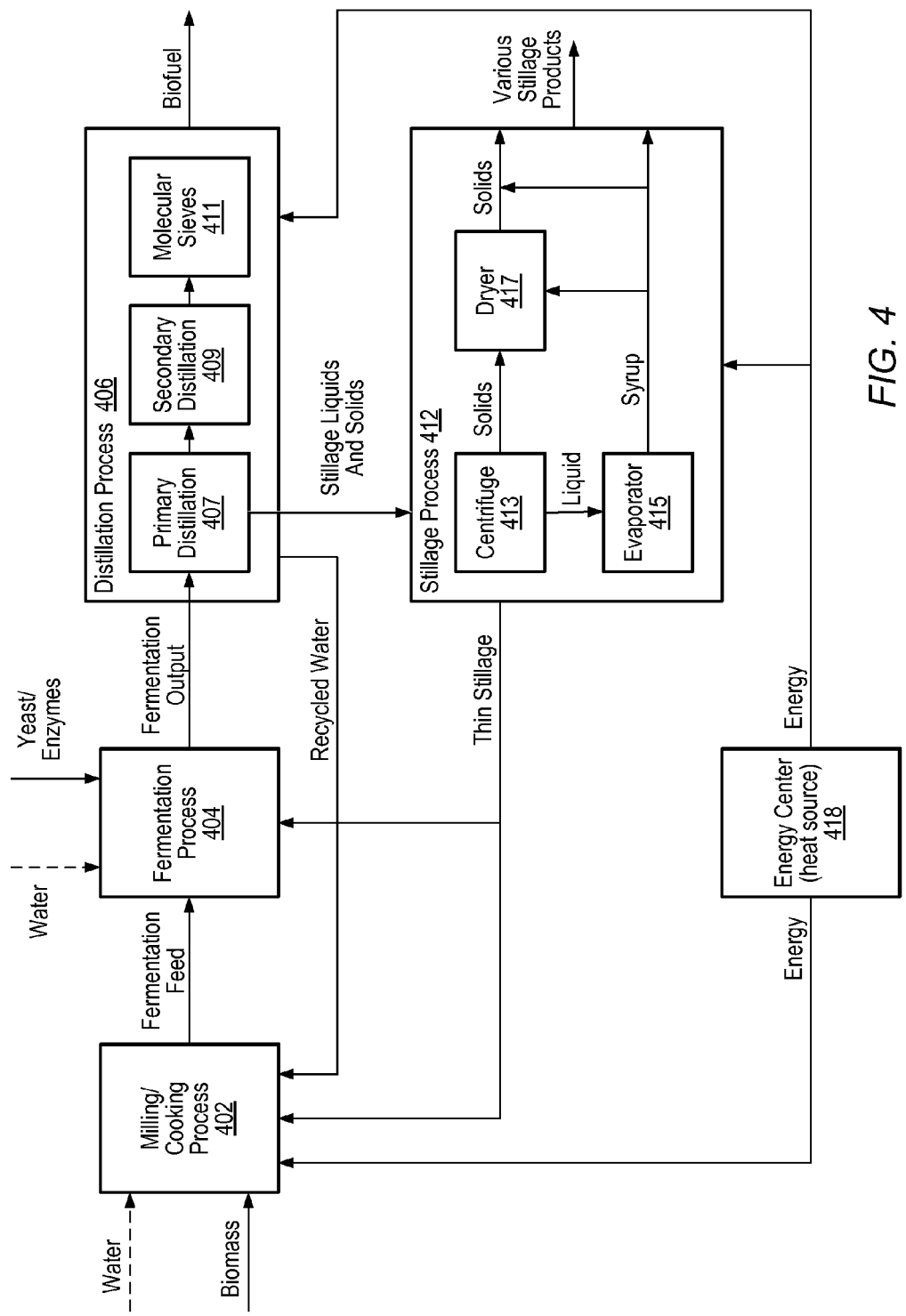
FIG. 4 illustrates an exemplary high-level processing flow schematic of plant sections of a biofuel processing plant, according to one embodiment.

FIG. 4 illustrates an exemplary high-level processing flow schematic of sub-processes of a biofuel production process, according to one embodiment. It should be noted that the particular components and processes shown are meant to be exemplary only, and are not intended to limit embodiments of the invention to any particular set of components or processes.

As FIG. 4 indicates, a milling/cooking process 402 may: receive water, biomass, energy (electrical and/or thermal), recycled water, and/or recycled thin stillage; mill the biomass; cook the mixture; and output a biomass slurry (referred to as a fermentation feed) to a fermentation process 404. The fermentation process 404 may: receive the biomass slurry, water, yeast, enzymes, and recycled thin stillage; ferment the mixture; and output fermentation products to a distillation process 406. The distillation process 406 may: receive the fermentation products, remove water and stillage (liquid and solid stillage) from the fermentation products in a one to three step process (e.g., primary distillation 407, secondary distillation 409, and/or molecular sieves (dryers) 411), recycle water removed from the fermentation products to the milling/cooking process 402, output the liquid and solid stillage to a stillage process 412, and output biofuel products. The stillage process 412 may: receive the liquid and solid stillage, process the liquid and solid stillage (utilizing one or more of centrifuge dryers 413, other dryers 417, and/or evaporators 415) to produce and output various stillage products, and recycle thin stillage liquid to the fermentation process 404 and the milling/cooking process 402. An energy center 418 may provide electric power and heat (steam) to the various sub-processes as shown in FIG. 4.

One or more of the processes described above may be managed and controlled via model predictive control (MPC) utilizing a dynamic multivariate predictive model that may be incorporated as a process model in a dynamic predictive model-based controller. Model predictive control of a sub-process of a biofuel production process is described below, first for a generic sub-process and then in more detail for integrated control of distillation and dehydration subprocesses.

MPC Applied to a Sub-Process of a Biofuel Production Process

Various embodiments of systems and methods for applying model predictive control (MPC) to a biofuel production process are described below. In this approach to biofuel production, a dynamic multivariate predictive model may be incorporated as a process model in a dynamic predictive model-based controller. This MPC system may project or predict what will happen in the production process (e.g., in the near future) based on the dynamic prediction model and recent process history, including, for example, recent operating conditions or state values. This projection or prediction may be updated or biased based on received current process information, specified objectives, and/or system or method constraints. Control algorithms may be used to recursively or iteratively estimate the best current and future control adjustments on the model inputs to achieve a desired output path. Targets set on the dynamic model outputs may be compared to how that output may behave over a predictive future horizon and the best available controllable model input adjustments may be estimated to best achieve the controller targets.

It should be noted that the biofuel or biofuels produced by embodiments of the methods described herein may be any biofuel generated from biomass, and that the types of biomass contemplated may be of any type desired, including, but not limited to, grains (e.g., corn, wheat, rye, rice, etc.), vegetables (e.g., potatoes, beats, etc.), canes (e.g., sugarcane, sorghum, etc.), and other recently living organisms and/or their bi-products.

Figure 5:
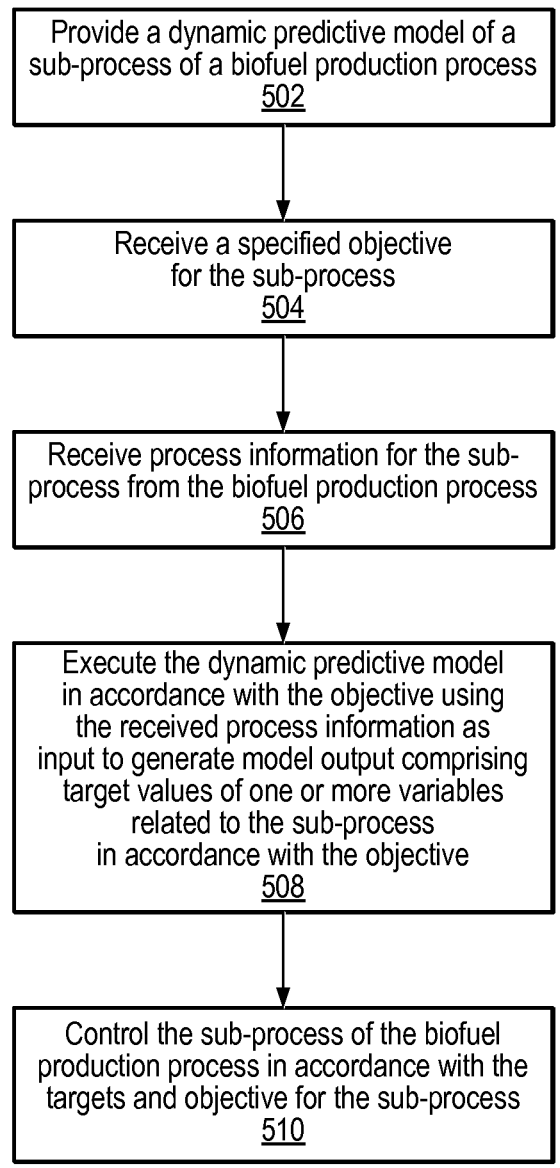
FIG. 5 is a high-level flowchart of a method for managing a sub-process of a biofuel production process utilizing model predictive control, according to one embodiment.

FIG. 5 is a high-level flowchart of a computer-implemented method for managing a sub-process of a biofuel production process utilizing model predictive control (MPC), according to one embodiment. As used herein, the term biofuel refers to one or more biofuel products output from a biofuel production process. It should be noted that embodiments of the method of FIG. 5 may be used with respect to any sub-process of a biofuel production process desired (e.g., milling/cooking, fermentation, distillation, and/or stillage processing), as well as combinations of such sub-processes. In various embodiments, some of the method elements shown may be performed concurrently, in a different order than shown, or may be omitted. Additional method elements may also be performed as desired. As shown, this method may operate as follows.

In 502, a dynamic multivariate predictive model (also referred to as a dynamic predictive model) of a sub-process of a biofuel production process may be provided. In other words, a model may be provided that specifies or represents relationships between attributes or variables related to the sub-process, including relationships between inputs to the sub-process and resulting outputs of the sub-process. Note that the model variables may also include aspects or attributes of other sub-processes that have bearing on or that influence operations of the sub-process.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard MPC models (i.e., fitted models generated by functional fit of data), or hybrid models using any combination of the above models.

In 504, an objective for the sub-process may be received. The objective may specify a desired outcome, result, behavior, or state, of the sub-process, such as, for example, a desired throughput, quality, efficiency, product profile, behavior, or cost, among others. In preferred embodiments, the objective may specify at least one targeted measurable attribute defining product quality for the sub-process (or the overall production process). Note that an objective may be a specific value, such as a specified percent solids for a fermentation feed, a specified temperature of a fermentation vat, etc., or may be a specified extremum, i.e., a maximum or minimum of an attribute, such as, for example, minimizing cost, maximizing production, etc.

It should be noted that as used herein, the terms "maximum", "minimum", and "optimum", may refer respectively to "substantially maximum", "substantially minimum", and "substantially optimum", where "substantially" indicates a value that is within some acceptable tolerance of the theoretical extremum, optimum, or target value. For example, in one embodiment, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations the control system will generally attempt to achieve optimum operation, i.e., operate at a targeted value or constraint (max or min) as closely as possible.

Moreover, in some embodiments, an objective may include multiple components, i.e., may actually comprise a plurality of objectives and sub-objectives. In some embodiments, the objective may involve multiple variables, e.g., a ratio of variables. Moreover, in some embodiments, there may be a global objective, e.g., maximize production or profit, and multiple sub-objectives that may in some cases be at odds with the global objective and/or one another.

In 506, process information for the sub-process of the biofuel production process may be received. In other words, information related to the sub-process may be received, e.g., from the sub-process (or from other portions of the biofuel production process that influence the sub-process), and/or from other sources, e.g., a laboratory, inferred property models (that model variables that are not readily measurable), external systems, or any other source as desired. This information generally includes data from one or more sensors monitoring conditions of and in the sub-process (e.g., temperatures, pressures, flow rates, equipment settings, and so forth), although any other information germane to the sub-process may be included as desired (e.g., constraints to which the sub-process may be subject, ambient conditions of the biofuel process, economic or market data, and so forth).

In 508, the model may be executed in accordance with the objective for the sub-process using the received process information as input, to generate model output comprising target values for one or more manipulated variables related to the sub-process in accordance with the objective for the sub-process. In other words, the model may be executed with the received process information as input, and may determine target values of one or more controllable attributes of the sub-process in an attempt to meet the specified objective for the sub-process (which could be a global objective for the entire biofuel production process). For example, in an embodiment where the objective is to maximize output for the sub-process, the model may determine various target values (e.g., sub-process material input flows, temperatures, pressures, and so forth) that may operate to maximize the output. As another example, in an embodiment where the objective is to minimize waste for the sub-process, the model may determine target values that may operate to minimize waste for the sub-process, possibly at the expense of total output. In a further example, the objective may be to maximize profit for the entire production process, where maximizing output and minimizing waste may be two, possibly competing, sub-objectives, e.g., included in the objective.

In some embodiments, the execution of the model in 508 may include executing the model in an iterative manner, e.g., via an optimizer, e.g., a nonlinear optimizer, varying manipulated variable values (which are a subset of the model inputs) and assessing the resulting model outputs and objective function, to determine values of the manipulated variables that satisfy the objective subject to one or more constraints, e.g., that optimize the sub-process subject to the constraints, thereby determining the target values for the manipulated variables.

In 510, the sub-process of the biofuel production process may be controlled in accordance with the corresponding targets and objective for the sub-process. Said another way, a controller coupled to the dynamic multivariate predictive model may automatically control various (controllable) aspects or variables of the sub-process according to the target values output by the predictive model to attempt to achieve the specified objective.

The method of FIG. 5 may be repeated, e.g., at a specified frequency, or in response to specified events, so that the process may be monitored and controlled throughout a production process, or throughout a series of production processes. In some embodiments, the period or frequency may be programmed or varied during the production process (e.g., an initial portion of a production process may have longer repetition periods (lower frequency), and a critical portion of a production process may have shorter repetition periods (higher frequency)).

In some embodiments, a system implementing the control techniques disclosed herein may include a computer system with one or more processors, and may include or be coupled to at least one memory medium (which may include a plurality of memory media), where the memory medium stores program instructions according to embodiments of the present invention. In various embodiments, the controller(s) discussed herein may be implemented on a single computer system communicatively coupled to the biofuel plant, or may be distributed across two or more computer systems, e.g., that may be situated at more than one location. In this embodiment, the multiple computer systems comprising the controller(s) may be connected via a bus or communication network.

Figure 6:
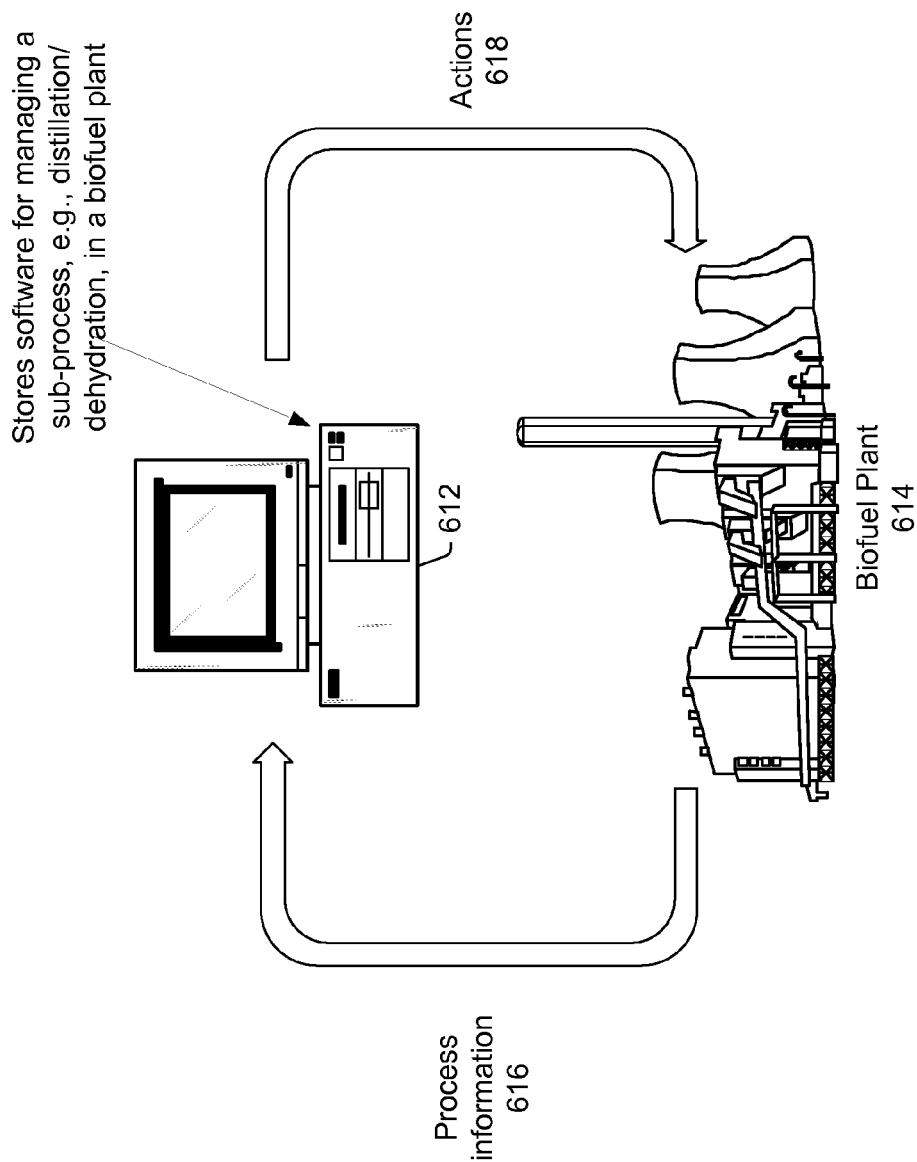
FIG. 6 is a simplified view a system for performing model predictive control of a sub-process, e.g., distillation/dehydration, in a biofuel production process, according to one embodiment.

FIG. 6 illustrates a simplified view of an automated control system for a biofuel production plant 614. As shown, the system may include one or more computer systems 612 which interact with the biofuel plant 614 being controlled. The computer system 612 may represent any of various types of computer systems or networks of computer systems which execute software program(s) according to various embodiments of the invention. As indicated, the computer system stores (and executes) software for managing a sub-process, e.g., distillation/dehydration, in the biofuel plant 614. The software program(s) may perform various aspects of modeling, prediction, optimization and/or control of the sub-process. Thus, the automated control system may implement predictive model control of the sub-process in the biofuel plant or process. The system may further provide an environment for making optimal decisions using an optimization solver, i.e., an optimizer, and carrying out those decisions, e.g., to control the plant.

One or more software programs that perform modeling, prediction, optimization and/or control of the plant 614 (particularly, the sub-process, e.g., distillation/dehydration process) may be included in the computer system 612. Thus, the system may provide an environment for a scheduling process of programmatically retrieving process information 616 relevant to the sub-process of the plant, and generating actions 618, e.g., control actions, to control the sub-process, and possibly other processes and aspects of the biofuel plant or process.

The one or more computer systems 612 preferably include a memory medium on which computer programs according to the present invention are stored. The term "memory medium" is intended to include various types of memory or storage, including an installation medium, e.g., a CD-ROM, or floppy disks, a computer system memory or random access memory such as DRAM, SRAM, EDO RAM, Rambus RAM, etc., or a non-volatile memory such as a magnetic medium, e.g., a hard drive, or optical storage. The memory medium may comprise other types of memory as well, or combinations thereof. In addition, the memory medium may be located in a first computer in which the programs are executed, or may be located in a second different computer which connects to the first computer over a network. In the latter instance, the second computer provides the program instructions to the first computer for execution.

Also, the computer system(s) 612 may take various forms, including a personal computer system, mainframe computer system, workstation, network appliance, Internet appliance or other device. In general, the term "computer system" can be broadly defined to encompass any device (or collection of devices) having a processor (or processors) which executes instructions from a memory medium.

The memory medium (which may include a plurality of memory media) preferably stores one or more software programs for performing various aspects of model predictive control and optimization. The software program(s) are preferably implemented using component-based techniques and/or object-oriented techniques. For example, the software program may be implemented using ActiveX controls, C++ objects, Java objects, Microsoft Foundation Classes (MFC), or other technologies or methodologies, as desired. A CPU, such as the host CPU, executing code and data from the memory medium comprises a means for creating and executing the software program according to the methods or flowcharts described below. In some embodiments, the one or more computer systems may implement one or more controllers, as noted above.

Figure 7A:
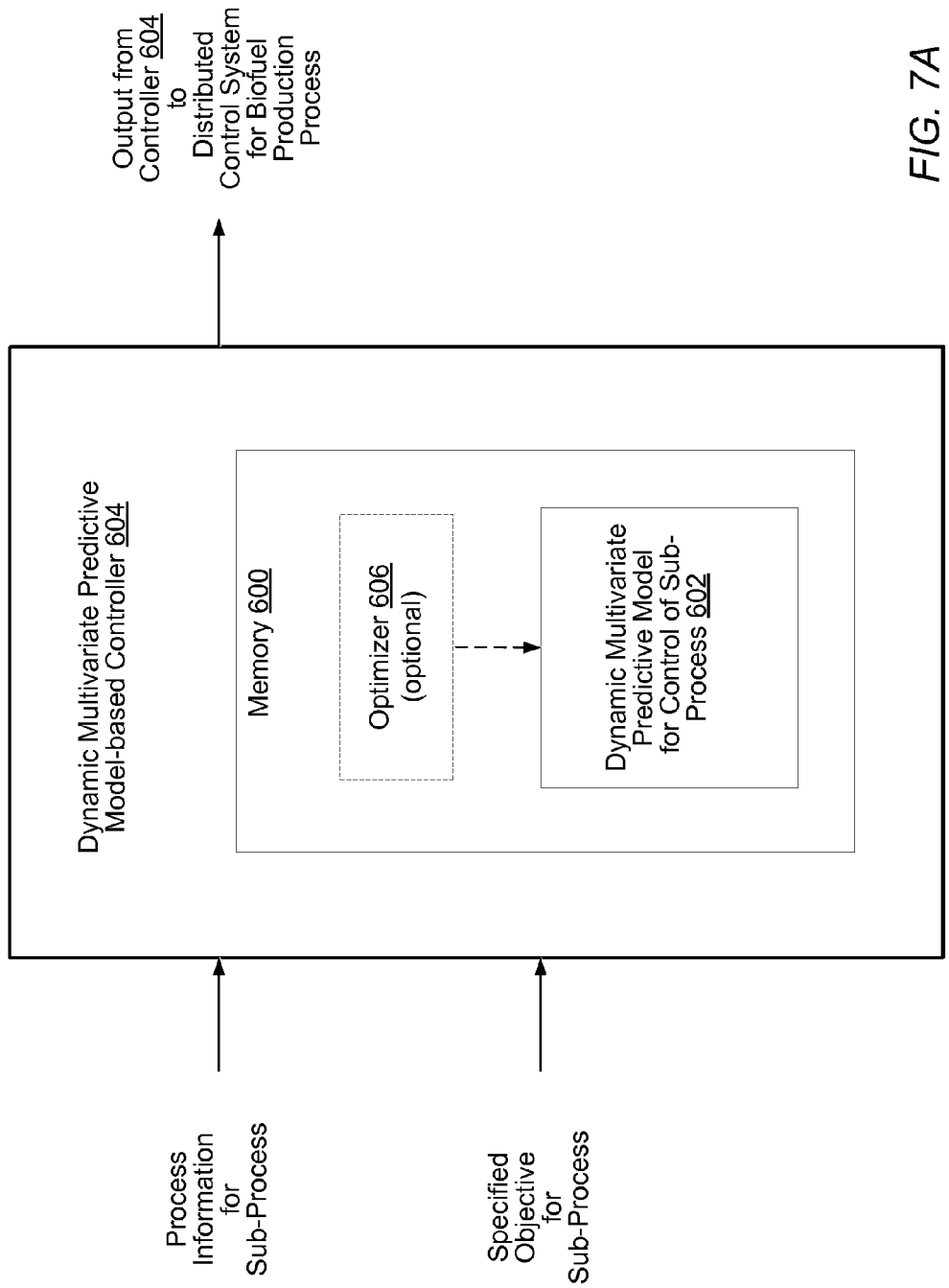
FIG. 7A is a high-level block diagram of a system for managing a sub-process of a biofuel production process utilizing model predictive control, according to one embodiment.

FIG. 7A illustrates an exemplary system for managing a sub-process of a biofuel production process, which may implement embodiments of the method of FIG. 5. The system may comprise: 1) a dynamic multivariate predictive model 602 (e.g., a predictive control model of a sub-process in the biofuel production process) stored in a memory 600; and 2) a dynamic predictive model-based controller 604 coupled to the memory 600.

As described above in more detail with respect to FIG. 5, the controller 604 may be operable to: receive an objective for a sub-process, receive process information related to the sub-process from the biofuel production process (possibly including information from a laboratory and/or inferred property models), execute the model in accordance with the objective for the sub-process using the received corresponding process information as input, to generate model output comprising target values for one or more variables related to the sub-process in accordance with the objective for the sub-process. In addition, as described above with respect to FIG. 5 in more detail, the dynamic predictive model-based controller 604 may control the sub-process of the biofuel production process in accordance with the corresponding targets and objective for the sub-process. In one embodiment, the controller 604 may output the target values to a distributed control system (not shown in FIG. 7A) for the biofuel production plant. In some embodiments, the target values may include or be one or more trajectories of values over a time horizon, e.g., over a prediction or control horizon. Process information may include measurements of a plurality of process variables for the sub-process and other inter-related sub-processes, information on one or more constraints, and/or information about one or more disturbance variables related to the sub-process. Process information may be received from the distributed control system for the biofuel plant, entered by an operator, or provided by a program. For example, in addition to values read (by sensors) from the actual process, the process information may include laboratory results, and output from inferred property models, e.g., virtual online analyzers (VOAs), among other information sources.

In some embodiments, the memory 600 may be part of the controller 604. In other embodiments, the memory 600 may be separated from the controller 604 and connected via a bus or a communication network. In one embodiment, the memory 600 may include more than one memory, with different portions of the model 602 stored in two or more of the memories, e.g., via a storage area network, or other distributed system.

The following describes more specific embodiments of model predictive control of a sub-process of a biofuel production process according to the method of FIG. 5 and system of FIGS. 6 and 7A. Note, however, that the embodiments of the particular sub-process described are meant to be exemplary, and that such model predictive control may be applied to other embodiments of the described sub-process of the biofuel production process as desired.

Integrated MPC Control of Distillation and Dehydration Sub-Processes in a Biofuel Production Process An overview of the distillation and dehydration sub-processes (also referred to herein as distillation and dehydration processes, distillation and dehydration sub-process, or distillation/dehydration process) is presented, and then model predictive control as applied to the distillation and downstream dehydration processes or portions thereof is described.

Distillation and Dehydration Sub-Processes

As discussed above and illustrated in FIG. 4, the distillation units, which may include primary 407 and secondary 409 distillation towers, receive the output of the fermentation process (a mixture of biofuel, stillage, and water) and may separate the biofuel from the water and stillage. Stillage may be removed from the primary distillation units and sent to the stillage processing units 413. Energy may be provided to the distillation units from the energy center 418, and may be primarily used by one or more primary distillation towers 407. The energy may typically be delivered to the primary distillation towers in the form of a steam flow through heat exchangers (not shown in FIG. 4), but in some embodiments the steam flow may be added directly to the primary distillation units 407. Energy may also be recycled to the distillation units from other process flows or provided by other heat sources as needed or desired. The flashed overhead vapor from the primary distillation towers may be transferred to one or more secondary distillation towers 409 (also referred to as rectification and stripping columns). In the secondary distillation towers 409, energy may be provided by heat exchangers utilizing steam and/or heat recovery from other processes, such as the cooking process 402 and/or the stillage process 412 utilizing energy recovery streams. The overhead vapor from the primary distillation towers may be a high purity biofuel (such as an ethanol/water mixture) that may be distilled close to its azeotropic point, but generally below fuel specification requirements. The secondary distillation towers' bottom product stream may be primarily condensed water. This condensed water may be recycled back to the milling/cooking process 402.

The overhead vapor from the primary distillation units 407 and the secondary distillation units 409 may be routed to inventory tanks (not shown in FIG. 4), which may be used as surge reservoirs to regulate the feed flow rates between the distillation units and to the one or more dehydration units. The dehydration units may be molecular sieve units 411 or other downstream dehydration processing units (e.g., extractive distillation). Molecular sieves may compose or be comprised in an energy efficient process unit that operates in gas phase using a dehydration process known as pressure swing adsorption (PSA). If the biofuel is ethanol, it may be dehydrated in either the liquid or gas phase. In some embodiments, molecular sieve beds 411 may absorb water in the biofuel vapor so that the resulting biofuel product may have only a trace amount of water per biofuel specification. When a molecular sieve bed 411 becomes saturated with water, it is taken offline, replaced with a parallel regenerated bed, and then placed back online. The offline beds may be regenerated under conditions that release the moisture and allow the beds to dry and be ready for future online use. PSA regeneration times may be adjusted to affect the efficiency and capacity of the molecular sieve beds 411. The biofuel product may then be sent to final storage in product inventory tanks (not shown in FIG. 4) and/or for additional processing.

Below are described various systems and methods for using model predictive control to improve the yield, throughput, and/or energy efficiency of biofuel distillation and dehydration sub-processes, in accordance with specified objectives. These objectives may be set and various portions of the process controlled continuously to provide real-time control of the production process. The control actions may be subject to or limited by plant and external constraints.

Figure 7B:
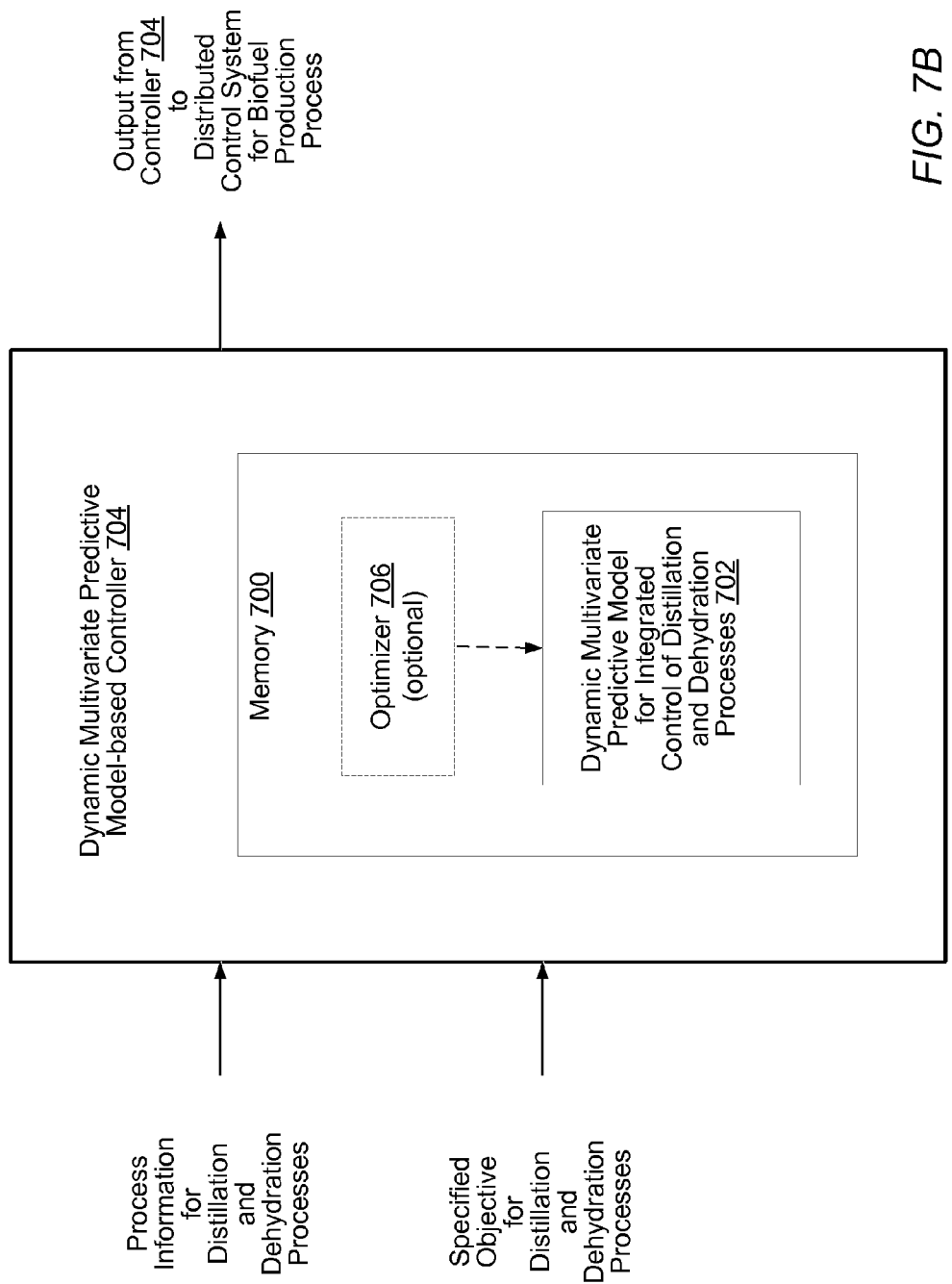
FIG. 7B is a high-level block diagram of a system for managing a distillation and dehydration sub-process of a biofuel production process utilizing model predictive control, according to one embodiment.
Figure 8:
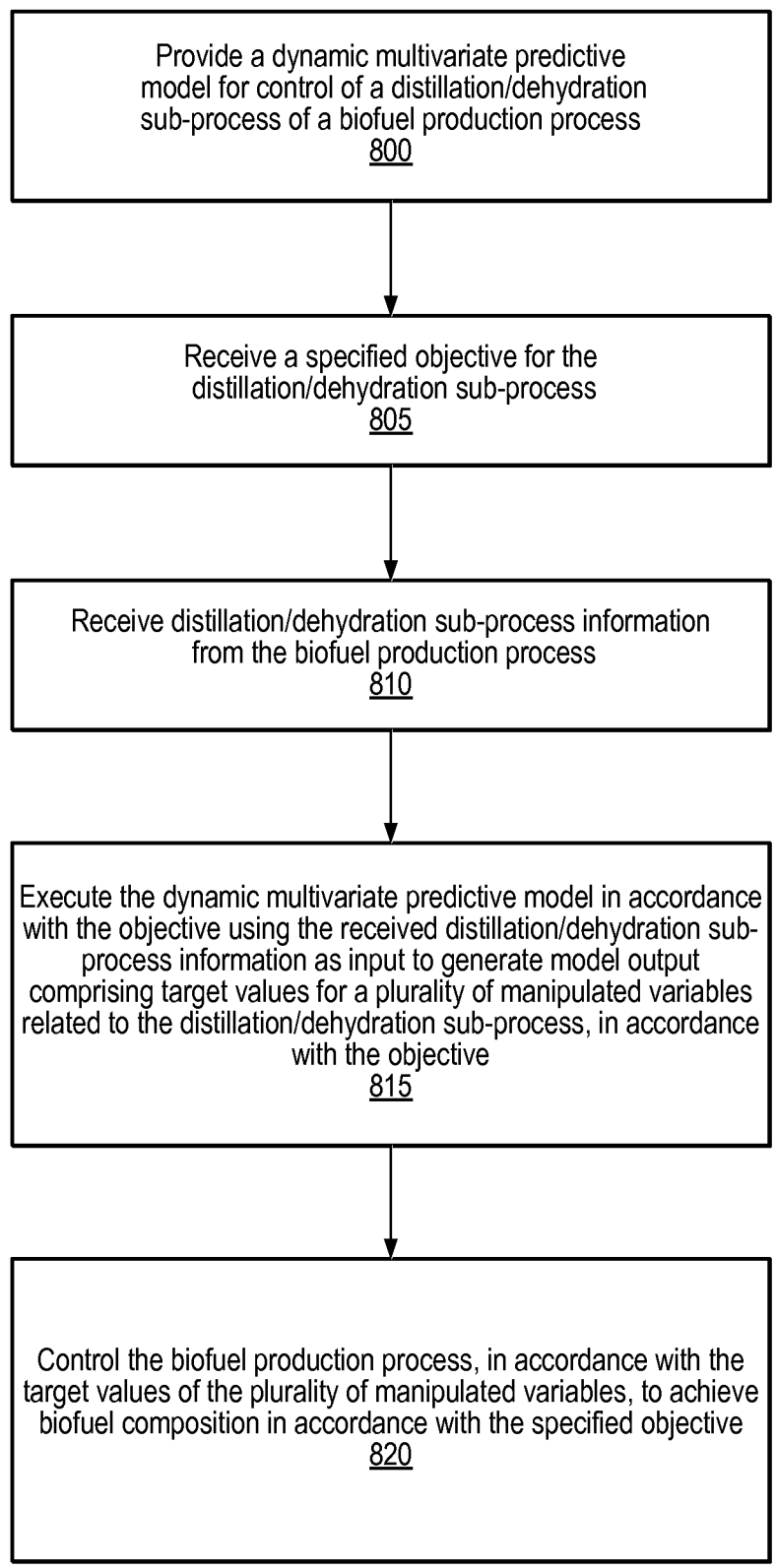
FIG. 8 is a high-level flowchart of a method for managing a distillation and dehydration sub-process of a biofuel production process utilizing model predictive control, according to one embodiment.

FIGS. 7B and 8 are directed to model predictive control of distillation and dehydration sub-processes in a biofuel production process (e.g., the distillation process 406 in FIG. 4). More specifically, FIG. 7B is a high-level block diagram of one embodiment of a system for integrated management of the distillation and dehydration sub-processes utilizing model predictive control to manage biofuel product quality and other objectives of the distillation and dehydration sub-processes in a biofuel production process. FIG. 8 is a high-level flowchart of one embodiment of a method for integrated management of the distillation and dehydration sub-processes utilizing model predictive control, where the distillation and dehydration sub-process provides biofuel and stillage outputs for a biofuel production process.

Any of the operations and controllable variables of the above described distillation and dehydration processes may be managed or controlled using model predictive control techniques. Below are described various exemplary systems and methods for doing so, although it should be noted that the particular operations and variables discussed are meant to be exemplary, and that any other aspects of the distillation and dehydration processes may also be managed using model predictive control as desired.

FIG. 7B—System for MPC Control of Distillation and Dehydration Sub-Processes

As shown in FIG. 7B, in one embodiment, a system for integrated management of biofuel distillation and dehydration processes of a biofuel production process may include: an integrated dynamic multivariate predictive model of the distillation and dehydration processes 702 stored in a memory 700, and a dynamic predictive model-based controller 704 (also referred to as a dynamic multivariate predictive model-based controller) coupled to the memory 700. In one embodiment, the controller 704 may be or include a computer system with one or more processors. In one embodiment, the controller 704 may be distributed across two or more computer systems situated at more than one location of the biofuel plant, and in this embodiment, the multiple computer systems comprising the controller 704 may be connected via a bus or communication network. In some embodiments, the memory 700 may be part of the controller 704. In other embodiments, the memory 700 may be separated from the controller 704 and connected via a bus or a communication network. In one embodiment, the memory 700 may include more than one memory, with different portions of the model 702 stored in two or more of the memories. In some embodiments, a separate model for each of the distillation process and the dehydration process may be provided, and the controller 704 may separately control the distillation process and the dehydration process. In still other embodiments, a first controller may control the distillation process and a second controller may control the dehydration process.

The dynamic multivariate predictive model-based controller 704 may be executable to: receive process information related to the distillation and downstream dehydration process from the biofuel production process (possibly including information from a laboratory and/or inferred property models), receive a specified objective for the distillation and dehydration processes, e.g., at least one targeted measurable attribute defining product quality for the distillation and dehydration processes, and execute the integrated dynamic multivariate predictive model, to generate model output comprising target values (possibly trajectories, e.g., over a time horizon) for one or more manipulated variables related to the distillation and dehydration processes in accordance with the specified objective. The controller 704 may be operable to control the distillation and dehydration processes in accordance with the target values and the specified objective. In some embodiments, the integrated dynamic multivariate predictive model of the distillation and dehydration processes may include a dynamic multivariate predictive model of the distillation process, a dynamic multivariate predictive model of the dehydration process, and a model of variables that are functions of one or both the distillation and dehydration processes. In some embodiments, the integrated dynamic multivariate predictive model 702 may include a plurality of sub-models directed to or modeling different portions of the distillation and dehydration processes. In one embodiment, the controller 704 may output the target values to a distributed control system (not shown in FIG. 7B) for the biofuel production plant. Process information may include measurements (and/or derived or inferred values) of a plurality of process variables for the sub-process and other inter-related sub-processes, information on one or more constraints, and/or information about one or more disturbance variables related to the sub-process. Process information may be received from the distributed control system for the biofuel plant, entered by an operator, or provided by a program. For example, in addition to values read (by sensors) from the actual process, the process information may include laboratory results, and output from inferred property models, e.g., virtual online analyzers (VOAs), among other information sources.

In one embodiment, the process of providing energy to the primary 407 and secondary 409 distillation towers may be represented in the dynamic multivariate predictive model 702 of the distillation and dehydration processes. In this embodiment, the dynamic predictive model-based controller 704 may also be executable to measure and regulate the heat energy supplied to the primary 407 and secondary 409 distillation towers.

While the above embodiments are directed to managing distillation and dehydration in an integrated manner, in some embodiments, distillation and dehydration may be managed substantially separately, i.e., model predictive control techniques may be applied to each process separately. For example, in one embodiment of the invention, a system for managing a biofuel distillation process in a biofuel production process may include: a dynamic multivariate predictive model of the distillation process, and a dynamic predictive model-based controller coupled to the dynamic multivariate predictive model. The dynamic multivariate predictive model may be executable to: receive distillation process information from the biofuel production process, receive a specified objective for the distillation process, and generate model output comprising target values for a set of specified variables of the distillation process in accordance with the specified objective. The controller may be operable to control the distillation process in accordance with the target values and the specified objective. Thus, MPC techniques may be separately applied to the distillation process in a biofuel production process.

Similarly, with respect to the dehydration process (downstream from the distillation process), in still another embodiment of the invention, a system for managing a biofuel dehydration process in a biofuel production process may include: a dynamic multivariate predictive model of the downstream dehydration process, and a dynamic predictive model-based controller coupled to the dynamic multivariate predictive model. The dynamic multivariate predictive model may be executable to: receive downstream dehydration process information from the biofuel production process, receive a specified objective for the dehydration process, and generate model output comprising target values for a set of specified variables of the dehydration process in accordance with the specified objective. The controller may be operable to control the dehydration process in accordance with the target values and the specified objective. Thus, MPC techniques may be separately applied to the dehydration process in a biofuel production process.

As noted above, the integrated dynamic multivariate predictive model 702 may be incorporated as a process model in the dynamic predictive model-based controller 704, and may be executed to provide target values for manipulated variables. In one embodiment, an optimizer program 706 may be stored in the memory 700 (shown as an optional element in FIG. 7B). In this embodiment, the controller 704 utilizes the optimizer 706 to execute the integrated dynamic multivariate predictive model in an iterative manner to generate or determine an optimum set of the target values in accordance with the objective for or over a specified time horizon. In this particular case, the optimum set of target values may be calculated by estimating the best, i.e., optimal or near optimal, current and future adjustments to values for the manipulated variables, e.g., over a specified period of time, i.e., a control or prediction horizon.

Model Predictive Control (MPC) may facilitate this best-case (i.e., optimal or near-optimal) achievement of projected future events, and may also enable multivariate balancing, so that, for example, levels across a series of tanks (e.g., fermentation output holding tanks) may be controlled to achieve optimal or near optimal results within process (and/or other, e.g., economic, regulatory, etc.) constraints even with a transient imbalance due to coordination of batch (e.g., fermentation) and continuous (e.g., distillation) operations. An MPC solution may have relative weighting factors to balance trade offs between competing objectives. For example, a tank level may be allowed to swing relatively freely within safe or comfortable operating regions (e.g., a tank level that is not nearly empty or nearing overflow). However, if a tank level forecast estimates that it may be nearly empty or near to over-filling, then different limit weighting may be used to avoid exceeding safe or comfortable operating states.

FIG. 8—Method for MPC Control of Distillation and Dehydration Sub-Processes

Embodiments of a method for integrated management of biofuel distillation and dehydration sub-processes of a biofuel production process are presented below. In one embodiment, as illustrated in FIG. 8, the method may include providing a dynamic multivariate predictive model for integrated control of the distillation and dehydration processes 800 (also referred to herein as the distillation/dehydration sub-process); receiving a specified objective for the distillation/dehydration sub-process 805; receiving distillation/dehydration sub-process information from the biofuel production process 810; executing the dynamic multivariate predictive model in accordance with the objective using the received distillation/dehydration sub-process information as input, to generate model output comprising target values for a plurality of manipulated variables related to the distillation/dehydration sub-process, in accordance with the objective 815; and controlling the biofuel production process, including water and/or biomass flow rates related to the fermentation feed of the biofuel production process, in accordance with the target values for the plurality of manipulated variables to achieve biofuel composition in accordance with the specified objective 820.

Various embodiments of the method stated above are discussed below in more detail. FIG. 8 is a high-level flowchart of a computer-implemented method for managing a sub-process of a biofuel production process utilizing model predictive control (MPC), according to one embodiment. In various embodiments, some of the method elements shown may be performed concurrently, in a different order than shown, or may be omitted. Additional method elements may also be performed as desired. In some embodiments an integrated model for both the distillation and the dehydration processes is utilized. In other embodiments, separate models are used for each process. As detailed in FIG. 8, this method may operate as follows.

Provide a Model

In 800 of FIG. 8, an integrated dynamic multivariate predictive model of the distillation/dehydration sub-process of a biofuel production process may be provided. In other words, a model may be provided that specifies or represents relationships between attributes, inputs, and/or other variables of the distillation/dehydration sub-process as related to biofuel composition (the outputs of the distillation/dehydration sub-process). Note that the model variables may also include aspects or attributes of other sub-processes that have bearing on or that influence operations of this sub-process.

The model may be of any of a variety of types. For example, the model may be linear or nonlinear, although for many complex processes, a nonlinear model may be preferred. Other model types contemplated include fundamental or analytical models (i.e., functional physics-based models, also referred to as first-principles models), empirical models (such as neural networks or support vector machines), rule-based models, statistical models, standard MPC models (i.e., fitted models generated by functional fit of data), or hybrid models using any combination of the above models. For example, in some embodiments where a hybrid approach is used, the integrated dynamic multivariate predictive model may include a fundamental model (e.g., a model based on chemical and/or physical equations) plus one or more of: a linear empirical model, a nonlinear empirical model, a neural network, a support vector machine, a statistical model, a rule-based model, or an otherwise empirically fitted model.

As is well known to those of skill in the art of model predictive control, a dynamic multivariate predictive model may include a set of process mathematical relationships that includes steady state relationships (e.g., primary distillation tower feed flow=primary distillation tower+secondary distillation tower (side-stripper) bottom flow), and also includes the time lag relationship for each parameter change to be realized in the output (e.g., a one gallon increase in primary distillation tower feed flow may immediately cause a change to primary distillation tower column bottom flow, but it may take 32 minutes for the full effect to occur and the bottom flow to come to a new steady state. At the secondary tower a one gallon increase in primary distillation tower feed flow may cause a change after 5 minutes of delay time, and a new steady state may be achieved in the overhead product flow and the bottom flow after 60 minutes of delay time). A great variety of dynamic relationships may be possible, and each relationship between variables may characterize or capture how one variable affects another, and also how fast the affects occur or how soon an effect will be observed at another location.

The model may be created from a combination of relationships based on available data such as: vessel volumes and fundamental dynamic and gain relationships, sufficiently available and moving plant historic process data, and supplementary plant testing on variables that cannot be identified from the two previous steps. Models may be customized to the plant layout and design, critical inventories, plant constraints and measurements, and controllers available to manage variables. Moreover, in some embodiments, external factors, such as economic or regulatory factors, may be included or represented in the model. In preferred embodiments, the dynamic multivariate predictive model may be a multivariable predictive control model.

An important characteristic of a dynamic model may be to identify when a control variable will change as a result of a change in one or more manipulated variables. In other words, the model may identify the time-response (e.g., time lag) of one or more attributes of the distillation/dehydration sub-process with respect to changes in manipulated variables. For example, once a controller adjusts pump speeds there may be a certain time-dependent response before observing an effect at a tank being filled. This time-dependent response may be unique for each independent controller (i.e., flow rates may vary because of differences in system variables (e.g., piping lengths, tank volumes, etc.) between the control actuator and flow sensor and the pump location).

Distillation feed tank levels and individual feeds to distillation units may be managed through calculations of the dynamic model, but there may be other process disturbances that may be unmeasured. For example, consider a situation where a level starts to rise out of balance with filling demand, e.g., because of manual plant changes (e.g., scheduled equipment cleaning that involves draining and/or filling one or more specific tanks)—the dynamic model may be made aware of an imbalance so that corrective actions may be made gradually to avoid dramatic or critical consequences. This may be an issue for many of the tanks that have both batch and continuous plant operations in sequence. Specific tanks may be used to provide storage capacity to facilitate balancing and avoid continuous out-of-control operations after every batch action. Because batch vessels drain rapidly, specific tank levels may be difficult to maintain in automatic level control. Thus, real-time receipt of current vessel and material balance information (flows and levels) may provide an update on current equipment status and the execution of the dynamic model may enable projections to be made to avoid both emptying/over-filling vessels and emergency large flow moves to correct imbalances.

In one embodiment, the integrated dynamic multivariate predictive model may include inferential models (also referred to as property approximators or virtual online analyzers (VOAs)). An inferential model is a computer-based model that calculates inferred quality properties from one or more inputs of other measured properties (e.g., process stream or process unit temperature(s), flow(s), pressure(s), concentration(s), level(s), etc.). For example, in one embodiment, these inferential models may compute the real-time properties of one or more properties from a list of properties comprising: primary distillation tower biofuel concentration in the bottom product stream, secondary distillation tower biofuel concentration in the overhead product stream, secondary distillation tower biofuel concentration in the bottom product stream, product stream off the molecular sieve units, and/or product stream quality off an extractive distillation, among others. In one embodiment, the integrated dynamic multivariate predictive model may be subdivided into different portions, and stored in a plurality of memories. The memories may be situated in different locations of the biofuel plant. The controller may communicate with the memories utilizing a communication system.

Receive a Specified Objective

In 805 of FIG. 8, a specified objective for the distillation/dehydration sub-process specifying target production of the biofuel output of the distillation and dehydration processes may be received.

A specified objective for the distillation/dehydration sub-process may include a desired behavior, attribute, or result of the distillation/dehydration sub-process (e.g., at least one targeted measurable or modelable attribute defining product quality for the biofuel output). For example, in some embodiments, specifying target production may include specifying one or more of: a target composition of the biofuel output of the distillation and dehydration processes, a production rate of the biofuel output of the distillation and dehydration processes (e.g., production rate of one or more distillation and dehydration units), or a target feed rate of the distillation and dehydration processes (i.e., input feed rate of one or more distillation and dehydration units).

In one embodiment, the specified objective may include one or more of: one or more operator specified objectives; one or more predictive model specified objectives; one or more programmable objectives; a target feed rate to the distillation units; one or more cost objectives; one or more product quality objectives; one or more equipment maintenance objectives; one or more equipment repair objectives; one or more equipment replacement objectives; one or more economic objectives; a target throughput for the biofuel production process; one or more objectives in response to emergency occurrences; one or more dynamic changes in product inventory information; one or more dynamic changes in product quality information; and/or one or more dynamic changes in one or more constraints on the biofuel production process, among others.

In some embodiments, the objective for the distillation/dehydration sub-process may be specified by a human operator and/or a program, and in some embodiments the objective may include one or more sub-objectives. The sub-objectives may include one or more of: combined feed rate to primary distillation units, individual feed rates to each primary distillation unit, heating load of primary distillation units, flow rate of non-fermentable solids output, rate of loss of biofuel into the non-fermentable solids output from the primary distillation units (also referred to as towers), distillation base ethanol concentration of output of primary distillation units, water content of the biofuel stream off the secondary distillation towers, rate of loss of biofuel in condensed water output from the secondary distillation units, water content in one or more output biofuel products, flow rates and inventories of one or more output biofuel products, and/or purity specification of one or more output biofuel products.

In some embodiments, the specified objective may comprise an objective function. The objective function may specify a set of objective values or relationships corresponding to each of one or more sub-objectives.

In some embodiments, constraint information specifying one or more constraints may also be received. For example, in some embodiments, the objective may include constraint information specifying the one or more constraints, i.e., limitations on various aspects, variables, or conditions, related to the distillation/dehydration sub-process, although in other embodiments, the constraint information may be separate and distinct from the specified objective. In one embodiment, the constraint information may include dynamic constraint information. In one embodiment, the one or more constraints may include one or more of: equipment constraints, capacity constraints, temperature constraints, pressure constraints, energy constraints, market constraints, economic constraints, regulatory constraints, and/or operator imposed constraints, among others. For example, in one embodiment, a constraint on operation of the secondary distillation tower may relate to pumping limitations on any of the various sections of the distillation tower (e.g., top section to side stripper, side stripper bottom pump, reflux pump, and/or overhead product pump). In situations where an objective is to maximize or maintain biofuel production rates, or product quality at certain target rates, this objective may drive a pump to its maximum or minimum limit, and the objective may then be compromised due to equipment/pump limits.

As another example, a constraint on operation of the secondary distillation tower may relate to tower separation problems as measured by a difference in pressure measured between (or across) any of the various sections of the distillation tower (e.g., top section to mid section, mid section to bottom section, and/or top section to bottom section). For example where a high column section pressure drop implies liquid or vapor phase column flooding (and equipment flow limitations), the column feed rate may not be maximized, but constrained to operate within a comfortable or safe range of operating pressure drop.

In one embodiment, the one or more constraints may also include equipment constraints comprising one or more of: fermentation equipment capacity limits that limit fermentation process output feed rates; equipment constraints that limit distillation feed capacity; operating limits for one or more pumps in the distillation units; operational status of pumps (online or offline); tank capacities; inventory tank level limits that limit feed rates to the distillation units; surge tank level or pumping limits that limit output flow rates from the primary distillation units; surge tank level or pumping limits that limit feed rates to the secondary distillation units operating limits for tank pressures; operational status of tanks; stillage tank level limits that limit output flow rates of stillage from the distillation units, distillation equipment offline; pump speed, valve position, or other controller output limits within the distillation or dehydration system; operating limits for valve pressures; operating limits for valve temperatures; equipment amp limits; operating limits for pipe pressures; pressure drop limits implying column flooding in liquid or vapor phase within the distillation section or piping sections; column pressure or pressure control capability limits; limits of distillation and/or dehydration equipment that limit moisture extraction and/or processing capacity flow rates; limits of operating pressure of the distillation and/or dehydration equipment that limit unit feed rate and/or biofuel purification; heating capacity limits that impact heat input to primary distillation units, secondary distillation units, and/or dehydration units; and/or efficiency of dehydration units due to absorption limits; among others. Thus, in some embodiments of the invention, the dynamic multivariate predictive model may specify relationships between distillation feed rates and equipment constraints, where the constraint information may include one or more equipment constraints of the biofuel production process.

In one embodiment, the dynamic multivariate predictive model may comprise a multivariate predictive model that represents relationships between the one or more constraints, the objective, including any sub-objectives, and the plurality of manipulated variables.

Receive Process Information

In 810 of FIG. 8, distillation/dehydration sub-process information may be received from the biofuel production process. The process information may include measurements of one or more control variables and one or more manipulated variables related to the distillation/dehydration sub-process and one or more variables of other processes that may impact the distillation/dehydration sub-process, as well as information from inferential models, laboratory results, etc. The measured variables may include any of: distillation unit feed rates; distillation feed temperature; heat input to the primary distillation units; heat input to the secondary distillation units; heat input to dehydration units; output flow rate of non-fermentable solids; the loss of biofuel into stillage (which is the product from the bottom of the primary distillation towers); the water content of the biofuel stream off the secondary distillation towers; the loss of biofuel to the secondary distillation tower's bottom product stream; column reflux of the distillation units; pump speed, valve position, or other controller output within the distillation or dehydration system; pressure drop within the distillation section or piping sections; column pressure; distillation base biofuel concentration of output of primary distillation units; biofuel product composition from one or more primary distillation units, biofuel product composition from one or more secondary distillation units; biofuel product composition from one or more dehydration units; process heating limits of the distillation\dehydration units; pressure limits of the distillation/dehydration process units; pressure drop limitation of the vaporized feed in the dehydration units; limits of the dehydration feed systems; water content of the one or more output biofuel products; purity specification of one or more output biofuel products; and/or the inventory of one or more output biofuel products, among others. The process information may be communicated to the controller from a distributed control system.

In some embodiments, distillation/dehydration sub-process information may include one or more of: fluid levels, operational status, and capacity limits for one or more biofuel vapor surge tanks; feed rate to primary distillation units, flow rates of one or more output biofuel products, water content of the one or more output biofuel products, purity specification of one or more output biofuel products, flow rate of non-fermentable solids output, distillation feed temperature, heat input to primary distillation units, heat input to secondary distillation units, heat input to dehydration units, biofuel output composition from one or more primary distillation units, biofuel output composition from one or more secondary distillation units, biofuel output composition from one or more dehydration units, output flow rate of non-fermentable solids, rate of loss of biofuel into the output of non-fermentable solids, rate of loss of biofuel in water stream output of the secondary distillation units, distillation base ethanol concentration of output of primary distillation units, and/or inventory amounts of one or more biofuel products, among others.

Execute the Model

In 815 of FIG. 8 the dynamic multivariate predictive model may be executed in accordance with the objective using the received distillation/dehydration sub-process information as input, to generate model output comprising target values for a plurality of manipulated variables related to the distillation/dehydration sub-process, in accordance with the objective.

In some embodiments, the specified objective may comprise an objective function. The objective function may specify a set of objective values corresponding to each of one or more sub-objectives. Executing the integrated dynamic multivariate predictive model may further comprise an optimizer executing the integrated dynamic multivariate predictive model in an iterative manner to solve the objective function, where solving the objective function generates the target values for the plurality of manipulated variables in accordance with the objective.

As noted above, in one embodiment, constraint information may be received, e.g., separately, or as part of the objective. In this embodiment, the dynamic multivariate predictive model may be executed in accordance with the objective using the received distillation/dehydration sub-process information and the one or more constraints as input, to generate model output in accordance with the objective and subject to the one or more constraints.

As also noted above, in one embodiment, the constraint information may be equipment constraints. In this embodiment, executing the dynamic multivariate predictive model may comprise executing the dynamic multivariate predictive model using the received distillation/dehydration sub-process information and received information related to the one or more equipment constraints as input to generate model output in accordance with the objective and subject to the one or more equipment constraints.

As noted above, in some embodiments, the execution of the model may include executing the model in an iterative manner, (e.g., via an optimizer, such as a nonlinear optimizer), varying manipulated variable values (e.g., feed rate to primary distillation units, distillation feed temperature, heat input to the primary distillation units, heat input to the secondary distillation units, heat input to dehydration units, etc.) and assessing the resulting model outputs and objective function, to determine values of the manipulated variables that optimally satisfy the objective subject to one or more constraints, thereby determining the target values for the manipulated variables.

Control the Process

In 820 of FIG. 8, the biofuel production process may be controlled in accordance with the target values for the plurality of manipulated variables to achieve biofuel composition in accordance with the specified objective, e.g., subject to specified constraints.

In one embodiment, controlling the biofuel production process may include controlling the flow rates of the distillation feed, which may include operating the distillation feed flow controllers coupled to the dynamic model, and/or operating the distillation feed flow controllers coupled to the biofuel production rate target. For example, distillation feed flow may be adjusted to manage throughput to a target production rate for the plant and/or the dynamic model distillation feed may be restricted to feeds within which acceptable biofuel quality can be achieved.

In one embodiment, controlling the biofuel production process may include controlling the primary distillation tower heat balance, which may include or utilize one or more of: a direct measurement of the primary distillation tower heat load, a proxy measurement of temperature such as a measurement of delta T (change in temperature) in the primary distillation tower, an operator or computer entered heat load control objective, a computer calculation of adjustments to the distillation feed rate, and/or a computer calculation of adjustments to heating rate or heat content.

In one embodiment, controlling the biofuel production process may include model predictive control of the loss of biofuel into stillage, which may include or utilize one or more of: a measure of loss of biofuel in stillage by a measurement via an instrument or by an inferential model, operator or computer entered biofuel in stillage concentration control objective, computer calculation and adjustments of distillation feed rate, and/or computer calculation and adjustments of heating rate or heat content.

In one embodiment, controlling the biofuel production process may include model predictive control of the water content of biofuel from the secondary distillation tower, which may include or utilize one or more of: a measure of loss of biofuel moisture by an instrument (e.g., a density meter) or an inferential model, operator or computer entered biofuel moisture measurement off the secondary distillation tower control objective, computer calculation and adjustments of the distillation feed rate, computer calculation and adjustments of heating rate or heat content in the primary distillation tower, computer calculation and adjustments of secondary distillation tower reflux, and/or computer calculation and adjustments of secondary distillation tower heating (rate or heat content).

In one embodiment, controlling the biofuel production process may include model predictive control of the loss of biofuel to the secondary distillation tower's bottom product stream, which may include or utilize one or more of: a measure of loss of biofuel in the secondary distillation tower bottoms measured by an instrument, lab samples, or an inferential model, operator or computer entered "biofuel losses in secondary distillation tower" control objective, computer calculation and adjustments of distillation feed rate, computer calculation and adjustments of primary distillation tower heating rate or heat content, computer calculation and adjustments of secondary distillation tower reflux flow rates, and/or computer calculation and adjustments of secondary distillation tower heat rate or heat content.

In one embodiment, controlling the biofuel production process may include model predictive control of the inventory of biofuel, which may include or utilize one or more of: a measure of the inventory of one or more biofuel products, an operator or computer entered control objective for the inventory of one or more biofuel products, computer calculation and adjustments of distillation feed rates, computer calculation and adjustments of rectifier column reflux flow rates, computer calculation and adjustments of molecular sieve feed rates, computer calculation and adjustments of centrifuge feed rates, computer calculation and adjustments of heating rates or heat duty for the evaporator units, and/or computer calculation and adjustments of evaporator syrup draw rate (e.g., for embodiments where heat recovery from stillage process evaporator operation is integrated with energy consumption within the distillation and/or downstream dehydration operations (e.g., evaporator waste steam vapors are used to drive a column reboiler, or a molecular sieve product condenser is used to reboil a column or provide energy to a stillage evaporator)).

In one embodiment, controlling the biofuel production process may include model predictive control of the biofuel moisture quality, which may include or utilize one or more of: a measure of the biofuel moisture quality concentration, operator or computer entered biofuel moisture quality control objective, computer calculation and adjustments of molecular sieve vaporizer pressure, computer calculation and adjustments of molecular sieve pressure, computer calculation and adjustments of molecular sieve feed rate, computer calculation and adjustments of molecular sieve feed quality, and/or computer calculation and adjustment to molecular sieve PSA timing.

As with FIG. 5 above, in preferred embodiments, the method of FIG. 8 may be repeated, e.g., at a specified frequency, or in response to specified events, so that the process may be monitored and controlled throughout a production process, or throughout a series of production processes. In some embodiments, the period or frequency may be programmed or varied during the production process (e.g., an initial portion of a production process may have longer repetition periods (lower frequency), and a critical portion of a production process may have shorter repetition periods (higher frequency)). In some embodiments, the method may be repeated based at least partially on events, e.g., in response to specified conditions.

Additional Embodiments

In one embodiment, a computer-accessible memory medium (which may include a plurality of memory media) stores program instructions for an integrated dynamic multivariate predictive model of a distillation process and a dehydration process of the biofuel production process. The program instructions may be executable to perform: receiving an objective specifying at least one measurable attribute defining product quality of a biofuel output from the distillation and dehydration processes; receiving distillation and dehydration process information from the biofuel production process; and executing the dynamic multivariate predictive model in accordance with the objective using the distillation and dehydration process information as input to generate model output comprising target values for a plurality of manipulated variables related to the distillation and dehydration processes in accordance with the objective.

In this embodiment, the program instructions may be further executable to: control the distillation/dehydration sub-process, in accordance with the target values for the plurality of manipulated variables and the specified objective. More generally, the memory medium may store program instructions implementing embodiments of any of the methods described above.

Thus, various embodiments of the above model predictive control systems and methods may be used to manage a distillation/dehydration sub-process in a biofuel production process.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications. Note the section headings used herein are for organizational purposes only and are not meant to limit the description provided herein or the claims attached hereto.

We claim:

1. A computer-implemented method for integrated management of a biofuel production process, comprising:
   providing an integrated dynamic multivariate predictive model of distillation and dehydration processes of the biofuel production process, wherein the integrated dynamic multivariate predictive model models transient imbalances in material flows or levels between a batch fermentation process and a continuous distillation process;
   receiving an objective for the distillation and dehydration processes, wherein the objective comprises a target biofuel production rate;
   receiving process information, comprising distillation and dehydration process information, from the biofuel production process;
   executing the integrated dynamic multivariate predictive model to achieve the objective using the process information as input, thereby generating target values for a plurality of manipulated variables, wherein the target values comprise a target distillation feed flow rate; and
   controlling the biofuel production process, in accordance with the target values of the plurality of manipulated variables, wherein controlling the biofuel production process comprises controlling the distillation feed in accordance with the target distillation feed flow rate.

2. The method of claim 1, wherein said executing the integrated dynamic multivariate predictive model further comprises an optimizer executing the integrated dynamic multivariate predictive model in an iterative manner to generate a substantially optimum set of the target values in accordance with the objective for a specified time horizon.

3. The method of claim 1, wherein the dynamic multivariate predictive model comprises a fundamental model, and one or more of:
   a linear empirical model;
   a nonlinear empirical model;
   a neural network;
   a support vector machine;
   a statistical model;
   a rule-based model; or
   an empirically fitted model.

4. The method of claim 1,
   wherein the objective includes one or more sub-objectives;
   wherein the objective comprises an objective function;
   wherein the objective function specifies a set of objective values corresponding to each of the one or more sub-objectives; and
   wherein said executing the integrated dynamic multivariate predictive model further comprises an optimizer executing the integrated dynamic multivariate predictive model in an iterative manner to solve the objective function, wherein solving the objective function generates the target values for the plurality of manipulated variables in accordance with the objective for a specified time horizon.

5. The method of claim 4, wherein each of the objective values is a value type selected from a set of value types including: minimum value, maximum value, greater than a specified value, less than a specified value, and equal to a specified value, and wherein the objective function includes a combination of two or more value types.

6. The method of claim 1, wherein said executing the dynamic multivariate predictive model comprises an optimizer executing the dynamic multivariate predictive model in an iterative manner to generate a substantially optimum set of target values for a specified time horizon in accordance with the objective.

7. The method of claim 1, wherein controlling the biofuel production process further comprises controlling a balance of heat within one or more primary distillation towers utilizing one or more of: a direct measurement of the heat load for one or more primary distillation towers, a proxy measurement of temperature such as a measurement of temperature differences between locations within the one or more primary distillation towers, an operator or computer entered heat load control objective, a computer calculation of adjustments to the distillation feed rate, or a computer calculation of adjustments to heating rate or heat content.

8. The method of claim 1, wherein controlling the biofuel production process further comprises controlling a loss of biofuel into stillage utilizing one or more of: a measure of loss of biofuel in stillage by a measurement via an instrument or by an inferential model, an operator or computer entered control objective for concentration of biofuel in stillage, a computer calculation and adjustments of a distillation feed rate, or a computer calculation and adjustments of primary distillation tower heating rates or heat contents.

9. The method of claim 1, wherein controlling the biofuel production process further comprises controlling biofuel moisture content in the output from one or more secondary distillation towers utilizing one or more of: a measure of loss of biofuel moisture by an instrument, a measure of loss of biofuel moisture content by an inferential model, an operator or computer entered control objective for biofuel moisture content of the output of the one or more secondary distillation towers, computer calculation and adjustments of the distillation feed rate, computer calculation and adjustments of heating rate or heat content in one or more primary distillation towers, computer calculation and adjustments of secondary distillation tower reflux, or computer calculation and adjustments of secondary distillation tower heating rates or heat contents.

10. The method of claim 1, wherein controlling the biofuel production process further comprises controlling a loss of biofuel to bottom product streams from one or more secondary distillation towers utilizing one or more of: a measure of loss of biofuel in the bottom product streams as measured by an instrument, as measured in a lab samples, or as calculated from an inferential model; an operator or computer or computer entered control objective for biofuel losses in the bottom product streams, a computer calculation and adjustments of distillation feed rate, a computer calculation and adjustments of primary distillation tower heating rates or heat contents, a computer calculation and adjustments of secondary distillation tower reflux flow rates, or a computer calculation and adjustments of secondary distillation tower heating rates or heat contents.

11. The method of claim 1, wherein controlling the biofuel production process further comprises controlling the inventory of biofuel utilizing one or more of: a measure of the inventory of one or more biofuel products, an operator or computer entered control objective for the inventory of one or more biofuel products, a computer calculation and adjustments of distillation feed rates, a computer calculation and adjustments of rectifier column reflux flow rates, or a computer calculation and adjustments of molecular sieve feed rates.

12. The method of claim 1, wherein controlling the biofuel production process further comprises controlling the biofuel moisture quality utilizing one or more of: a measure of the biofuel moisture quality concentration, an operator or computer entered biofuel moisture quality control objective, a computer calculation and adjustments of molecular sieve vaporizer pressure, a computer calculation and adjustments of molecular sieve pressure, a computer calculation and adjustments of molecular sieve feed rate, a computer calculation and adjustments of molecular sieve fee quality, or a computer calculation and adjustment to molecular sieve pressure swing adsorption (PSA) timing.

13. The method of claim 1, further comprising:
receiving constraint information specifying one or more constraints, wherein said executing the integrated dynamic multivariate predictive model comprises executing the integrated dynamic multivariate predictive model in accordance with the objective using the received process information and the one or more constraints as input, thereby generating the target values for the plurality of manipulated variables in accordance with the objective and subject to the one or more constraints.

14. The method of claim 13, wherein the one or more constraints comprise one or more of: process constraints, equipment constraints, regulatory constraints, or economic constraints.

15. The method of claim 13, wherein the dynamic multivariate predictive model incorporates relationships between the one or more constraints, the objective, and the plurality of manipulated variables.

16. The method of claim 1, further comprising:
repeating the recited method steps with a specified frequency, utilizing updated process information and objectives, wherein the frequency is:
programmable; and/or
operator-determined.

17. The method of 16, wherein the frequency is determined by changes in process, equipment, regulatory, and/or economic constraints.

18. A system for management of a biofuel production process, comprising:
a dynamic predictive model-based controller comprising one or more processors; and
at least one memory medium coupled to the one or more processors;
wherein the at least one memory medium stores program instructions implementing a dynamic multivariate predictive model of distillation and dehydration processes of the biofuel production process, wherein the integrated dynamic multivariate predictive model models transient imbalances in material flows or levels between a batch fermentation process and a continuous distillation process;
wherein the one or more processors are operable to:
receive process information from the biofuel production process;

receive an objective for the distillation and dehydration processes, wherein the objective comprises a target biofuel production rate; and execute the dynamic multivariate predictive model, thereby generating target values for one or more manipulated variables, wherein the target values comprise a target distillation feed flow rate; and wherein the controller is operable to control the distillation and dehydration processes in accordance with the target values and the objective, wherein controlling the distillation and dehydration processes comprises controlling the distillation feed in accordance with the target distillation feed flow rate.

19. The system of claim 18, further comprising an optimizer program stored in one or more of the at least one memory medium, wherein the one or more processors are further operable to utilize the optimizer program to execute the dynamic multivariate predictive model in an iterative manner to generate a substantially optimum set of target values for a specified time horizon in accordance with the objective.

20. A computer-accessible memory medium that stores program instructions for dynamic model predictive control of a biofuel production process, wherein the program instructions are executable to perform:

receiving an objective from distillation and dehydration processes of the biofuel production process, wherein the objective comprises a target biofuel production rate;

receiving process information from the biofuel production process; and executing the dynamic multivariate predictive model to achieve the objective using the process information as input, thereby generating target values for a plurality of manipulated variables, wherein the target values comprise a target distillation feed flow rate;

wherein the target values for the plurality of manipulated variables are usable to control the distillation and dehydration process of the biofuel production process, and to correct for transient imbalances between a batch fermentation process and a continuous distillation process, wherein controlling the distillation and dehydration process of the biofuel production process comprises controlling the distillation feed in accordance with the target distillation feed flow rate.

21. The memory medium of claim 20, wherein the program instructions are further executable to control the distillation and dehydration processes in accordance with the target values and the objective.

22. The memory medium of claim 20, wherein the program instructions implement an optimizer, wherein the optimizer is executable to perform said executing the dynamic multivariate predictive model in an iterative manner to generate a substantially optimum set of target values for a specified time horizon in accordance with the objective.

* * * * *